US009821071B2

(12) United States Patent
Murthy et al.

(10) Patent No.: US 9,821,071 B2
(45) Date of Patent: Nov. 21, 2017

(54) OLIGOSACCHARIDE CONJUGATES FOR TARGETING BACTERIA AND USES RELATED THERETO

(71) Applicants: Emory University, Atlanta, GA (US); Georgia Tech Research Corporation, Atlanta, GA (US); Georgia State Research Foundation, Atlanta, GA (US)

(72) Inventors: Niren Murthy, Berkeley, CA (US); Eric Seth Gilbert, Atlanta, GA (US); Xinghai Ning, Athens, GA (US); Mark Goodman, Atlanta, GA (US); Bryan Stubblefield, Atlanta, GA (US)

(73) Assignees: Emory University, Atlanta, GA (US); Georgia Tech Research Corporation, Atlanta, GA (US); Georgia State University Research Foundation, Inc., Atlanta, GA (US)

( * ) Notice: Subject to any disclaimer, the term of this patent is extended or adjusted under 35 U.S.C. 154(b) by 81 days.

(21) Appl. No.: 14/190,928

(22) Filed: Feb. 26, 2014

(65) Prior Publication Data
US 2014/0219917 A1    Aug. 7, 2014

Related U.S. Application Data

(63) Continuation of application No. 13/979,382, filed as application No. PCT/US2012/021202 on Jan. 13, 2012, now abandoned.

(60) Provisional application No. 61/432,668, filed on Jan. 14, 2011.

(51) Int. Cl.
| *A61K 51/00* | (2006.01) |
| *A61M 36/14* | (2006.01) |
| *A61K 47/48* | (2006.01) |
| *A61K 49/00* | (2006.01) |
| *A61K 51/06* | (2006.01) |
| *A61K 45/06* | (2006.01) |
| *A61K 31/496* | (2006.01) |
| *C08B 31/00* | (2006.01) |
| *C08L 3/04* | (2006.01) |

(52) U.S. Cl.
CPC ........ *A61K 47/4823* (2013.01); *A61K 31/496* (2013.01); *A61K 45/06* (2013.01); *A61K 49/0021* (2013.01); *A61K 49/0032* (2013.01); *A61K 49/0054* (2013.01); *A61K 51/06* (2013.01); *A61K 51/065* (2013.01); *C08B 31/00* (2013.01); *C08L 3/04* (2013.01)

(58) Field of Classification Search
CPC .... A61K 51/00; A61K 51/0491; A61K 51/06; A61K 51/065; A61K 45/00; A61K 45/06; A61K 47/00; A61K 47/4823; A61K 47/26; A61K 49/00; A61K 49/0021; A61K 49/0032; A61K 49/0054; A61K 31/00; A61K 31/496; C08L 3/04; C08B 31/00
USPC .......... 424/1.11, 1.65, 1.73, 1.81, 1.85, 1.89, 424/9.1, 9.2, 9.3, 9.4, 9.5, 9.6; 514/23, 514/25, 35, 53, 54, 55, 56, 57, 58, 59, 60, 514/61
See application file for complete search history.

(56) References Cited

U.S. PATENT DOCUMENTS

| 5,569,366 | A | 10/1996 | Chen et al. |
| 5,902,795 | A * | 5/1999 | Toole .................... A61K 31/70 514/13.3 |
| 6,596,546 | B1 | 7/2003 | Jolley et al. |
| 7,196,073 | B2 | 3/2007 | Marciani |
| 7,563,433 | B2 * | 7/2009 | McBride .......... A61K 47/48746 424/1.11 |
| 8,501,154 | B2 | 8/2013 | Cheeseman et al. |
| 8,623,322 | B2 | 1/2014 | Norenberg et al. |
| 8,835,380 | B2 | 9/2014 | Ferguson et al. |
| 8,961,926 | B2 | 2/2015 | Low et al. |
| 9,005,577 | B2 | 4/2015 | Walsh et al. |
| 9,180,215 | B2 | 11/2015 | Low et al. |
| 9,402,925 | B2 | 8/2016 | Namavari et al. |
| 2004/0137525 | A1 | 7/2004 | Jolley et al. |
| 2010/0240878 | A1 | 9/2010 | Barbeau |
| 2014/0314671 | A1 | 10/2014 | Namavari et al. |

FOREIGN PATENT DOCUMENTS

| EP | 2651411 A2 | 10/2013 |
| WO | 2007011696 A8 | 2/2009 |
| WO | 2014043606 | 5/2014 |
| WO | 2014135590 A1 | 9/2014 |
| WO | 2015061540 A1 | 4/2015 |

OTHER PUBLICATIONS

Pajatsch et al, Carbohydrate Research, 1998, vol. 307, pp. 375-379.*
Fuchs P.C., et al., "PMX-522 (Polymyxin B-Dextran 70) Does Not Alter In Vitro Activities of 11 Antimicrobial Agents," Antimicrobial Agents and Chemotherapy 42(10), 1998, pp. 2765-2767.
Bordignon et al., The maltose ATP-binding cassette transporter in the 21st century-towards a structural dynamic perspective on its mode of action, Mol. Microbiol. 77(6):1354-66, 2010.
Crouzel et al., Recommendations for a practical production of [11C]methyl iodide, Appl. Radiat. Isot. Int. J. Appl. Instrum. Part A 38:601-603, 1987.

(Continued)

*Primary Examiner* — D L Jones
(74) *Attorney, Agent, or Firm* — Meunier Carlin & Curfman LLC

(57) ABSTRACT

This disclosure relates to conjugates for targeting bacteria and related uses. In certain embodiments, the disclosure relates to methods of transferring a molecule of interest into bacteria comprising mixing bacteria with a non-naturally occurring conjugate under conditions such that the conjugate is transported across the bacterial cell wall. Typically, the conjugate comprises an oligosaccharide and a molecule of interest. In certain embodiments, the molecule of interest may be a tracer or an antibiotic.

4 Claims, 15 Drawing Sheets

(56) References Cited

OTHER PUBLICATIONS

Jewett et al., Captive solvent methods for fast simple carbon-11 radioalkylations, New Trends in Radiopharmaceutical Synthesis, Quality Assurance and Regulatory Control, Plenum Press, New York, 387-391, 1991.
Jewett, A Simple synthesis of [11C]methyl triflate, Appl. Radiat. Isot. 43:1383-1385, 1992.
Marazano et al., Synthesis of methyl iodide 11C and formaldehyde-11C, Appl. Radiat. Isot. 28:49-52, 1977.
Thatiparti et al., Cyclodextrin Complexation for Affinity-Based Antibiotic Delivery, Macromol. Biosci. 10:82-90, 2010.
Watkins et al., A captive solvent method for rapid N-[11C] methylation of secondary amides application to the benzodiazepine, 4'-chlorodiazepam (R05-4864), Appl. Radiat. Isot. 39:441-444, 1988.
Wilson, Radiochemistry of Tracers for Neurotransmitter Receptor Studies. In: Quantitative Imaging: Neuroreceptors, Neurotransmitters, and Enzymes, Raven Press, New York; 19-35, 1990.
Wilson et al., In vivo evaluation of [11C] and [15F]-labeled cocaine analogues as potential dopamine transporter ligands for positron emission tomography, Nucl. Med. Biol. 23:141-146, 1996.
International Search Report and Written Opinion for PCT/US2012/21202 dated Aug. 27, 2012.
Azzopardi, et al., "Development and Validation of an In Vitro Pharmacokinetic/Pharmacodynamic Model to Test the Antibacterial Efficacy of Antibiotic Polymer Conjugates", Antimicrobial Agents and Chemotherapy, 2015, 59(4):1837-1843.
Eggleston, et al., "Molecular Imaging of Bacterial Infections in vivo: The Discrimination between Infection and Inflammation", Informatics, 2014, 1:72-99.
Ferguson, et al., "Dextrin—Colistin Conjugates as a Model Bioresponsive Treatment for Multidrug Resistant Bacterial Infections", Molecular Pharmaceuticals, 2014, 11:4437-4447.
Fuchs, et al., "PMX-622 (Polymyxin B-Dextran 70) Does Not Alter In Vitro Activities of 11 Antimicrobial Agents", Antimicrobial Agents and Chemotherapy, 1998, 42(10):2765-2767.
Glaudemans, et al., "The Use of F-FDG-PET/CT for Diagnosis and Treatment Monitoring of Inflammatory and Infectious Diseases", Clinical and Developmental Immunology, 2013, 623036:1-14.
Gowrishankar, et al., "Investigation of 6[18F]-Fluoromaltose as a Novel PET Tracer for Imaging Bacterial Infection", PLOS one, 2014, 9(9):1-6.
Kim, et al., "FDG PET/CT Imaging for LVAD Associated Infections", Cardiovascular Imaging, 2014, 7(8):839-842.
Lake, et al., "Pharmacodynamic Evaluation of the Neutralization of Endotoxin by PMX622 in Mice", Antimicrobial Agents and Chemotherapy, 2004, 48(8):2987-2992.
Love, et al., "Radionuclide Imaging of Inflammation and Infection in the Acute Care Setting", Seminars in Nuclear Medicine, 2013, 43(2):102-113.
Mokaleng, et al., "Synthesis, 68Ga-Radiolabeling, and Preliminary In Vivo Assessment of a Depsipeptide-Derived Compound as a Potential PET/CT Infection Imaging Agent", Biomed Research International, 2015, 284354:1-12.
Namavari, et al., "Synthesis of [18F]-labelled Maltose Derivatives as PET Tracers for Imaging Bacterial Infection", Mol. Imaging Biol., 2015, 17(2):168-176.
Rolle, et al., "ImmunoPET/MR imaging allows specific detection of Aspergillus fumigatus lung infection in vivo", PNAS, 2016, E1026-E1033.
Wang, et al., "Clinical Diagnosis of Bacterial Infection via FDG-PET Imaging", Canadian Chemical Transactions, 2013, 1(2):85-104.
Weinstein, et al., "Imaging Enterobacteriaceae infection in vivo with 18F-fluorodeoxysorbitol positron emission tomography", Science Translational Medicine, 2014, 6(259):259ra146.
"Maltose/Maltodextrin System of *Escherichia coli*: Transport, Metabolism, and Regulation", Microbiol and Molec Biol Reviews 62:1, 1998, 204-229.
Chen, et al., "Synthesis of Fluorous Tags for Incorporation of Reducing Sugars into a Quantitative Microarray Platform", Org Lett 10:5, 2008, 785-788.
Dippel, et al., "The Maltodextrin System of *Escherichia coli*: Metabolism and Transport", J Bacteriol 187:24, 2005, 8322-8331.
Fowler, et al., "Initial and Subsequent Approach for the Synthesis of <18> FDG", Seminars in Nuclear Med, Grune and Stratton 32:1, 2002, 6-12.
Hein, et al., "Click Chemistry, A powerful tool for pharmaceutical science", Pharma Research, Kluwer Academic Publishers 25:10, 2008, 2216-2230.
Hsu, et al., "MALDI-TOF and ESI-MS Analysis of Oligosaccharides Labeled with a New Multifunctional Oligosaccharide Tag", J Am Soc Mass Spectro, Elsevier Sci Inc 17:2, 2006, 194-204.
Huang, et al., "Carbohydrate microarray for profiling the antibodies interacting with Globo H tumor antigen", Proc Nat Acad Sci 103:1, 2006, 15-20.
Kato, et al., "Development of tetraphenylethylene-based fluorescent oligosaccharide probes for detection of influenza virus", Biochem Biophys Res Comm 394:1, 2010, 200-204.
Ning, et al., "Maltodextrin-based imaging probes detect bacteria in vivo with high sensitivity and specificity", Nat Mat 10:8, 2011, 62-607.
Ning, et al., "PET imaging of Bacterial Infections with Fluorine-18-Labeled Maltohexaose", Angewandte Chemie Int Ed 53:51, 2014,14096-14101.
Yu, et al., "Review of 18F-FDG synthesis and quality control", Biomed Imaging Intervention Journal, Univ of Malaya 2:4, 2006,1-11.
Supplementary Partial European Search Report issued in Application No. 12734757, dated Jun. 15, 2016.
Extended European Search Report issued in Application No. 12734757, dated Sep. 15, 2016.

* cited by examiner

OLIGOSACCHARIDE CONJUGATES FOR TARGETING BACTERIA AND USES RELATED THERETO

CROSS REFERENCE TO RELATED APPLICATIONS

This application is a continuation of U.S. patent application Ser. No. 13/979,382, filed Jul. 12, 2013, which is a 371 U.S. National Phase of International Application No. PCT/US2012/021202, filed Jan. 13, 2012, which claims the benefit of priority to U.S. Provisional Application No. 61/432,668, filed Jan. 14, 2011, the entire contents of which are incorporated herein by reference.

ACKNOWLEDGMENTS

This invention was made with government support under Grants NSF-EEC9731643, BES-0546962, and NIH-U01HL80711-01. The government has certain rights in the invention.

BACKGROUND

A major limitation preventing the effective treatment of bacterial infections is an inability to image them in vivo with accuracy and sensitivity. Consequently, bacterial infections can be diagnosed only after they have become systemic or have caused significant anatomical tissue damage, a stage at which they are challenging to treat owing to the high bacterial burden. Although contrast agents have been developed to image bacteria, their clinical impact has been minimal because they are unable to detect small numbers of bacteria in vivo, and cannot distinguish infections from other pathologies such as cancer and inflammation. There is therefore a great need for the development of contrast agents that can image small numbers of bacteria accurately in vivo.

Bacteria can utilize glycogen, starch, and amylose as carbon sources. Prior to transport through the cell membrane, these polysaccharides are hydrolyzed by the extracellular α-amylase into smaller maltodextrins, maltose and isomaltose. Maltose ABC importer (type I) of *Escherichia coli* enables the bacteria to feed on maltose and maltodextrins. Bordignon et al., Mol. Microbiol., 2010, 77(6):1354-66.

Positron emission tomography (PET) is nuclear medicine imaging technique that produces a two- or three-dimensional image in the body. The system detects pairs of gamma rays emitted indirectly by a positron-emitting radionuclide (tracer), which is introduced into the body on a biologically active molecule. 2-Deoxy-2-($^{18}$F)fluoro-D-glucose, an analogue of glucose, is a commonly used human tracer for PET imaging. The concentrations of tracer imaged then give tissue metabolic activity in terms of regional glucose uptake.

Beta-cyclodextrin has been contemplated for affinity based delivery of an antibiotic through non-covalent interactions. See Thatiparti & Recum, Macromol. Biosci., 2010, 10, 82-90.

SUMMARY

This disclosure relates to oligosaccharide conjugates for targeting bacteria and related uses. In certain embodiments, the disclosure relates to methods of transferring a molecule of interest into bacteria comprising mixing bacteria with a non-naturally occurring conjugate, wherein the conjugate comprises an oligosaccharide and a molecule of interest under conditions such that the conjugate is transported across the bacterial cell wall. In certain embodiments, the molecule of interest may be a tracer or an antibiotic.

With regard to any of the conjugates disclosed herein, the oligosaccharide may be a polysaccharide of greater than 2, 3, 4, 5, or 6 sugar oligomers which are typically isolated or substantially purified. In some embodiments, the polysaccharide comprises glucose oligomers, e.g., maltohexaose, a polysaccharide with 6 glucose oligomers. Typically, the glucose oligomers are linked by an alpha 1→4 covalent bond. In certain embodiments, the disclosure contemplates oligosaccharides of glucose oligomers and/or 2-deoxyglucose oligomers wherein one or more of the glucose monomers are substituted with a positron-emitting radionuclide $^{18}$F.

In certain embodiments, the disclosure relates to an imaging method comprising a) administering a tracer molecule conjugated to an oligosaccharide as disclosed herein to a subject; and b) scanning the subject for a physical property of the tracer molecule. Typically, the method further comprises the step of detecting the physical property of the tracer molecule and using a computer to create an image highlighting the location of the tracer molecule in the subject. The subject may be a human subject or other animal. In certain embodiments, the conjugates are used to enhance imaging techniques such as positron emission tomography (PET). An image of radioactive decay as a function of location for parcels may be constructed and plotted. The image shows the tissues in which the tracer has become concentrated.

In another embodiment, provided is a method of monitoring the level of bacteria within a body of a patient, the method comprising administering a pharmaceutical composition comprising any of the radiolabeled conjugates disclosed herein to a subject, and employing a nuclear imaging technique selected from the group consisting of positron emission tomography (PET) and single photon emission computed tomography (SPECT) for monitoring a distribution of the conjugate within the body or within a portion thereof.

In certain embodiments, the methods are capable of detecting bacteria at a CFU/g (colony-forming units per gram) of at or about a level of or less than $10^9$, $10^8$, $10^7$, $10^6$, or $10^5$. The conjugates have utility for both Gram negative and Gram positive bacteria.

In certain embodiments, the disclosure relates to methods of treating or detecting device-related infections or other infections involving surface-attached bacteria, or biofilms.

In certain embodiments, this disclosure relates to compositions comprising a tracer molecule conjugated to an oligosaccharide. In certain embodiments, the tracer molecule is a radioactive or positron-emitting radionuclide. The positron-emitting radionuclide may be selected from carbon-11, $^{11}$C, nitrogen-13, $^{13}$N, oxygen-15, $^{15}$O, fluorine-18, $^{18}$F, rubidium-82, and strontium-82. In certain embodiments, the tracer is a radioactive isotope such as tritium, $^3$H, carbon-14, $^{14}$C, sulfur-35, $^{35}$S, iodine-131, $^{131}$I, technetium-99m, $^{99}$mTc, $^{67}$Gallium, and $^{111}$In. In certain embodiments, the tracer molecule is fluorescent molecule. The fluorescent molecule may be a florescent dye, fluorescent protein, or quantum dot. The florescent molecule may comprise an aromatic ring.

In certain embodiments, the disclosure relates to methods comprising a) administering a composition comprising a positron-emitting radionuclide and oligosaccharide conjugate (such as an oligosaccharide of glucose) to a subject at risk of, suspected of, or diagnosed with a bacterial infection, and b) detecting gamma photos in an area of the subject. Typically the methods further comprising creating an image from the detected gamma photons.

In certain embodiments, the disclosure relates to methods of evaluating the effectiveness of an antibacterial therapy comprising administering a conjugate, wherein the conjugate comprises a tracer and oligosaccharide, to a subject before, during, or after an antibiotic therapy and detecting or measuring accumulation of the tracer in the subject. In certain embodiments, the method further comprises detecting or measuring a decrease in the accumulation of the tracer at a site in the subject at a predetermined time after administration and correlating it to a successful treatment of the subject. In certain embodiments, the method further comprises detecting or measuring an similar or increase in the accumulation of the tracer at the site in the subject at a predetermined time after administration and correlating a similar concentration or increased concentration to the ineffectiveness of the antibiotic therapy. In certain embodiments, the method further comprises changing the antibiotic therapy to an alternative antibiotic therapy. The increase, decrease, or similar accumulation may be made in reference to an evaluation in the site of a subject before, after, or during the administration of an antibiotic therapy. The successful or unsuccessful treatment may be recorded on a computer and reported to a medical professional or reported to the subject.

In certain embodiments the disclosure relates to methods of treating or preventing a bacterial infection comprising administering an effective amount of an isolated conjugate to a subject in need thereof wherein the isolated conjugate comprises an antibiotic and an oligosaccharide as disclosed herein. The isolated conjugate may optionally be administered in combination with another antibiotic.

In certain embodiments, the disclosure relates to compositions comprising an antibiotic conjugated to an oligosaccharide. The antibiotic may be selected from the group comprising of sulfonamides, carbapenems, penicillins, diaminopyrimidines, quinolones, beta-lactam antibiotics, cephalosporins, tetracyclines, notribenzenes, aminoglycosides, macrolide antibiotics, polypeptide antibiotics, nitrofurans, nitroimidazoles, nicotinin acids, polyene antibiotics, imidazoles, glycopeptides, cyclic lipopeptides, glycylcyclines, and oxazolidinones or other compounds. The antibiotic may be selected from dapsone, paraminosalicyclic, sulfanilamide, sulfamethizole, sulfamethoxazole, sulfapyridine, trimethoprim, pyrimethamine, nalidixic acid, norfloxacin, ciproflaxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, amoxicillin, ampicillin, azlocillin, carbenicillin, cloxacillin, dicloxacillin, flucloxacillin, hetacillin, oxacillin, mezlocillin, penicillin G, penicillin V, piperacillin, cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefinenoxime, cefodizime, cefoperazone, cefotaxime, cefotiam, cefpimizole, cefpiramide, cefpodoxime, cefteram, ceftibuten, ceftiofur, ceftiolen, ceftizoxime, ceftriaxone, cefoperazone, ceftazidime, cefepime, moxolactam, imipenem, ertapenem, meropenem, aztreonam, oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomicin, neomycin, netilmicin, streptomycin, tobramycin, azithromycin, clarithromycin, dirithromycin, erythromycin, roxithromycin, telithromycin, polymyxin-B, colistin, bacitracin, tyrothricin, notrifurantoin, furazolidone, metronidazole, timidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, chloramphenicol, clindamycin, colistin, fosfomycin, loracarbef, nitrofurantoin, procain, spectinomycin, timidazole, ramoplanin, teicoplanin, and vancomycin.

In certain embodiments, the disclosure contemplates compounds, derivatives, or substituted compounds disclosed herein.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Targeting Bacteria

A central problem in imaging bacterial infections is to develop targeting strategies that can deliver large quantities of imaging probes to bacteria. This has been challenging because typical imaging probes target the bacterial cell wall and cannot access the bacterial intracellular volume. Although numerous contrast agents have been developed to image bacteria, their clinical impact has been minimal because they are unable to detect small numbers of bacteria in vivo, and cannot distinguish infections from other pathologies such as cancer and inflammation. Within certain embodiments, the disclosure relates to maltodextrin-based imaging probes (MDPs), which can detect bacteria in vivo with a sensitivity two orders of magnitude higher than previously reported, and can detect bacteria using a bacteria-specific mechanism that is independent of host response and secondary pathologies.

Figure 1:
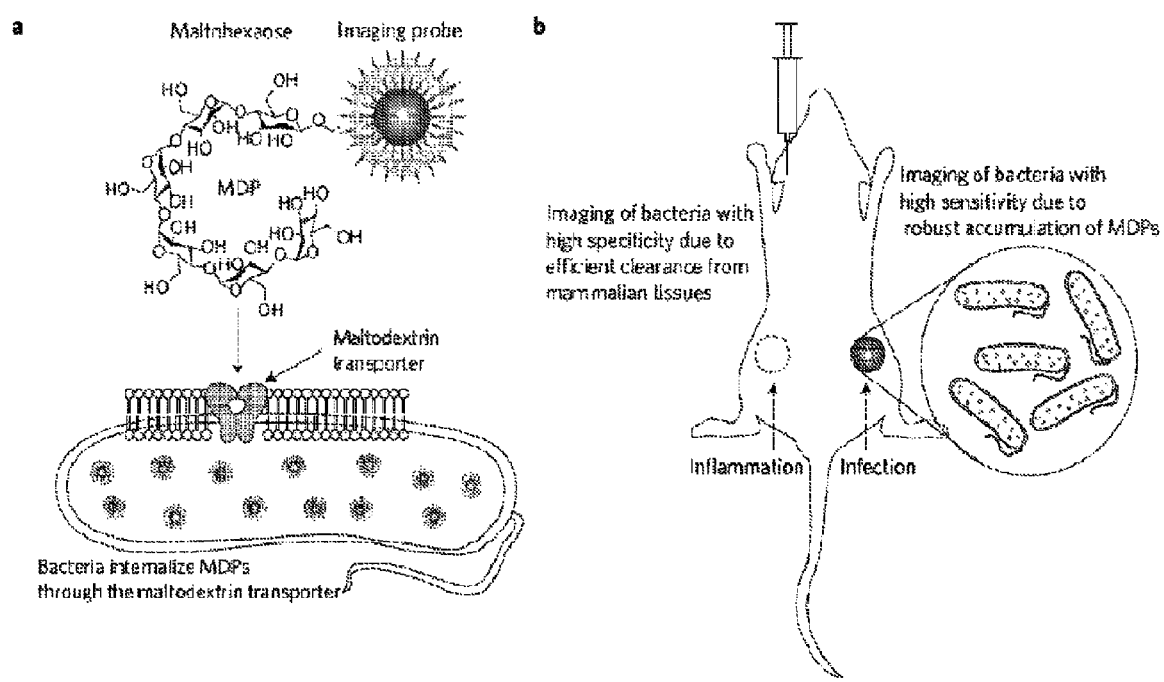
FIG. 1 illustrates certain embodiments of the disclosure. a, Chemical design of Maltodextrin-Based Imaging Probes (MDPs). MDPs are a family of contrast agents that target the maltodextrin transport pathway and can image bacteria in vivo. MDPs are composed of maltohexaose conjugated to an imaging probe. MDPs are internalized as a glucose source and are transported by bacteria at a high rate. Maltodextrin transporters are not present in mammalian cells and MDPs therefore also have specificity for bacteria. b, MDPs image bacteria in vivo with high sensitivity and specificity. MDPs are robustly internalized by bacteria but not by mammalian cells, and can therefore detect low numbers of bacteria in vivo and also distinguish between inflammation and bacterial infections.

In certain embodiments, MDPs are composed of a fluorescent dye conjugated to maltohexaose, and are rapidly internalized through the bacteria-specific maltodextrin transport pathway, endowing the MDPs with a unique combination of high sensitivity and specificity for bacteria. Certain MDPs selectively accumulate within bacteria at millimolar concentrations, and are a thousand-fold more specific for bacteria than mammalian cells. Furthermore, MDPs can image as few as $10^5$ colony-forming units in vivo and can discriminate between active bacteria and inflammation induced by either lipopolysaccharides or metabolically inactive bacteria Contrast agents that are robustly internalized through the bacteria-specific maltodextrin transporter and can image bacterial infections in vivo with improved sensitivity and specificity (see FIG. 1). Maltohexaose is a major source of glucose for bacteria and MDPs can therefore deliver millimolar concentrations of imaging probes into bacteria, making it possible to image low numbers of bacteria. MDPs also have high specificity for bacteria because mammalian cells do not express the maltodextrin transporter and cannot internalize contrast agents conjugated to maltohexaose. MDPs are typically composed of α(1→4)-linked glucose oligomers. Because MDPs are typically hydrophilic and membrane impermeable, they are efficiently cleared from uninfected tissues in vivo, leading to a low background. Furthermore, the lumen of intestinal tissues or the outer layers of the skin are not permeable to glucose oligomers. MDPs delivered systemically should therefore not be internalized by the resident bacterial microflora present in healthy subjects.

Figure 2:
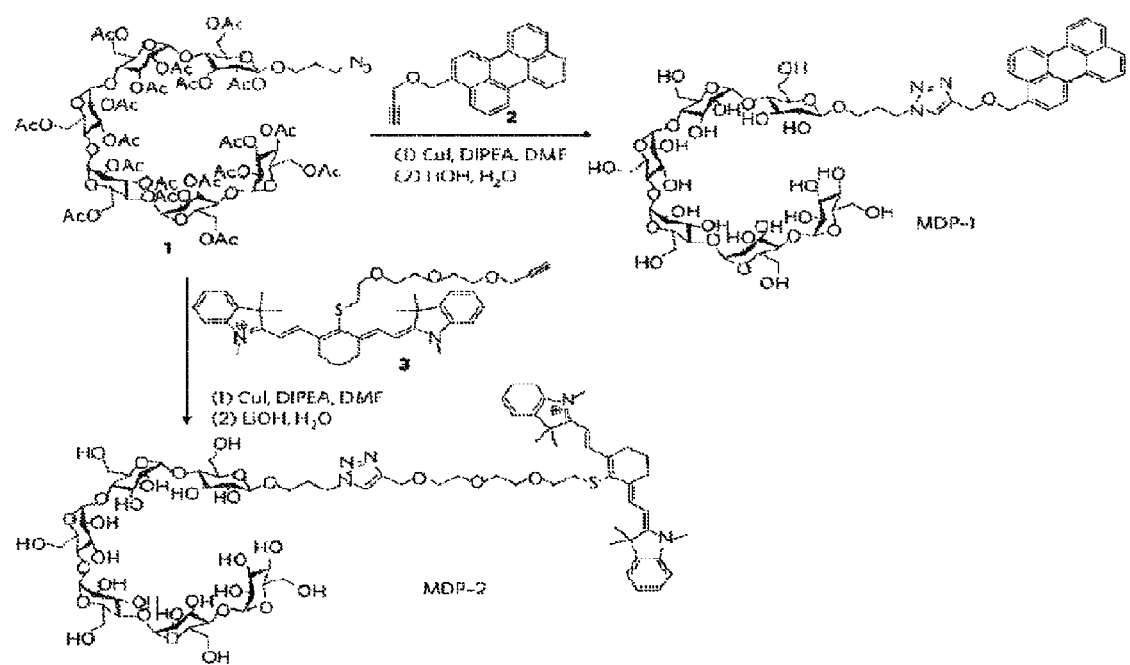
FIG. 2 schematically illustrates the preparation of certain embodiments of the disclosure. MDP-1 and MDP-2 were synthesized by conjugation of 1 with either 2 or 3 using the copper (I) catalyzed click reaction.

The bacterial imaging agents MDP-1 and MDP-2 were synthesized to image bacteria in vitro and in vivo, and are composed of maltohexaose conjugated to either perylene or IR786 (see FIG. 2). MDP-1 and MDP-2 were synthesized by clicking alkyne-functionalized fluorescent dyes onto an azide-functionalized maltohexaose.

Figure 3:
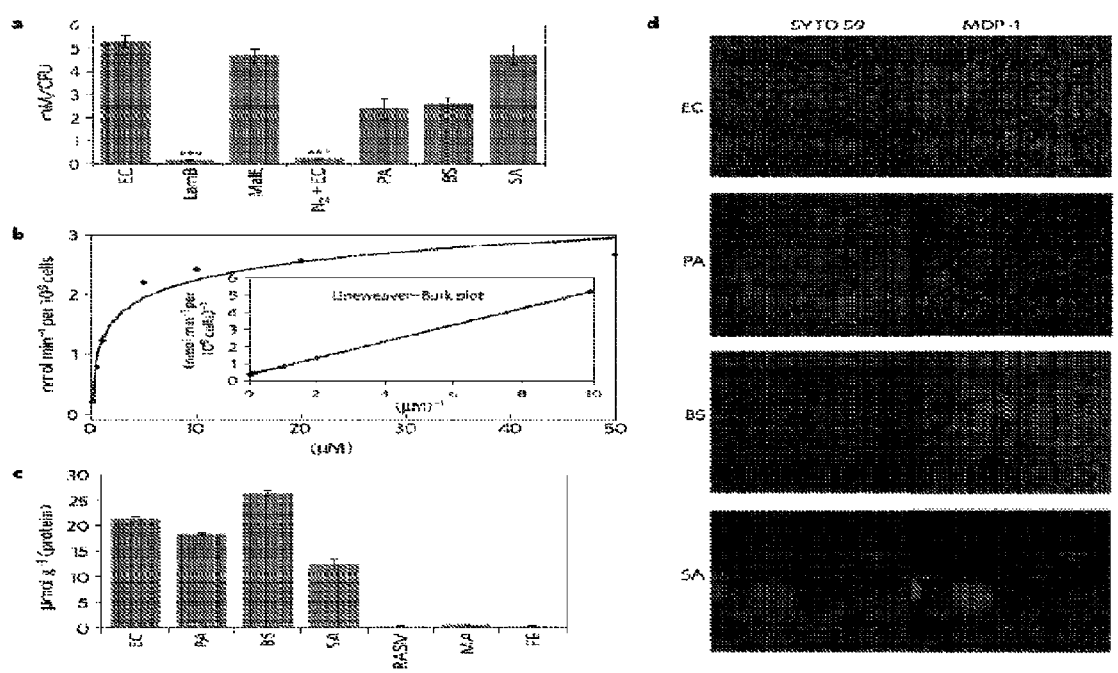
FIG. 3 shows data indicating MDPs have specificity for planktonic bacteria and bacterial biofilms. a, Histogram showing the levels of MDP-1 internalization. Gram-negative and gram-positive bacteria robustly internalize MDP-1. MDP-1 is robustly internalized by $E.\ coli$ (EC), $P.\ aeruginosa$ (PA), $B.\ subtilis$ (BS), $S.\ aureus$ (SA) and $E.\ coli$ MalE mutant strains (MalE). The uptake of MDP-1 in $E.\ coli$ LamB mutant strains (LamB) and metabolically inactive $E.\ coli$ (EC+$N_3$) is significantly reduced. Results are expressed as mean millimolar concentration per CFU±standard error of the mean (s.e.m.), for n=6 per group. The p values between the EC and LamB or EC+$N_3$ were determined by a one-way analysis of variance (ANOVA) using Bonferroni's post-hoc test, and were found to be statistically significant (p≤0.001). b, Plot showing that the uptake of MDP-1 in $E.\ coli$ is saturable and follows Michaelis-Menten kinetics, with a $V_{max}$ of 2.7 nmol min$^{-1}$ per $10^9$ cells and a $K_M$ of 1.3 μM. c, Histogram quantifying the level of MDP-1 transport. MDP-1 has high specificity for bacteria when compared with mammalian cells. Bacteria ($E.\ coli,\ P.\ aeruginosa,\ B.\ subtilis$ and $S.\ aureus$) transport MDP-1 at a rate three orders of magnitude faster than mammalian cells (rat aortic smooth muscle cells (RASMs), macrophages (MAs) and fibroblasts (FBs)). The results are expressed as mean micromoles per gram of protein±s.e.m. for n=6 per group. The p values between each group of bacteria and each group of mammalian cells were determined by a one-way ANOVA using Bonferroni's post-hoc test, and were found to be statistically significant (p≤0.001). d, Fluorescence micrographs showing that the biofilms (*E. coli, P. aeruginosa, B. subtilis* and *S. aureus*) robustly internalize MDP-1.

Maltodextrin transporters internalize their substrates at a robust rate in bacteria. The uptake of MDP-1 was evaluated in gram-positive and gram-negative bacteria, under aerobic and anerobic fermentative conditions. *Escherichia coli, Pseudomonas aeruginosa, Bacillus subtilis* and *Staphylococcus aureus* were incubated with a 20 μM concentration of MDP-1 for 1 h, washed with PBS, lysed, and the MDP-1 in the cellular supernatant was analyzed by fluorescence microscopy. FIG. 3a demonstrates that MDPs can deliver large quantities of imaging probes to bacteria, under both aerobic and anaerobic fermentative conditions. For example, *E. coli* internalized MDP-1 at a rate sufficient to generate millimolar intracellular concentrations, and followed Michaelis-Menten kinetics, with a V max of 2.7 nmol min$^{-1}$ per $10^9$ cells and a KM of 1.3 μM (shown in FIG. 3b). Furthermore, pathogenic bacteria such as *P. aeruginosa, S. aureus* and *B. subtilis* also robustly internalized MDP-1. This represents a targeting strategy that can deliver millimolar concentrations of an imaging probe to bacteria.

Oligosaccharide Conjugates, Derivatives, and Related Compounds

In certain embodiments, the disclosure relates to compounds of formula I,

A-E-G            Formula I or salts thereof wherein,
A is a oligosaccharide;
E is a linking group; and
G is an tracer, a drug, an antibiotic, an azide group, or other molecule of interest.

In certain embodiments, A is a oligosaccharide comprising glucose, a glucose derivative, and/or a substituted glucose oligomer.

In certain embodiments, E is triazole positioned between linking groups such as the following groups alone or in combination, ether, amine, amide, ester, carbonyl, thiol, dithiol, thiolester, aromatic, heteroaromatic, or hydrocarbon groups.

In certain embodiments, the disclosure relates to compounds of formula I with formula IA

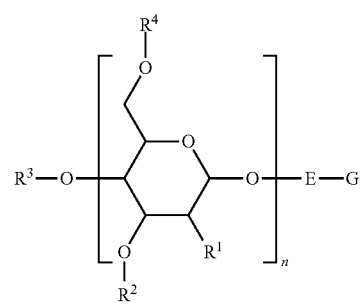

Formula IA or salts thereof wherein,
n is 2, 3, 4, 5, 6, 7, 8, 9, 10, 11, 12, 13, 14, or 15;
E is a linking group;
G is a molecule of interest such as a radionuclide, fluorescent moiety, an antibiotic, or an azide group;
$R^1$, $R^2$, $R^3$, and $R^4$, are each individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein each $R^1$, $R^2$, $R^3$, and $R^4$ are optionally substituted with one or more, the same or different, $R^5$;
$R^5$ is alkyl, halogen, nitro, cyano, hydroxy, amino, mercapto, formyl, carboxy, alkanoyl, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein $R^5$ is optionally substituted with one or more, the same or different, $R^6$; and
$R^6$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiment, n is 5 or 6 or more, or n is 3 or 4 or more.

In certain embodiments, R², R³, and R⁴ are hydrogen or alkanoyl optionally substituted with R⁵.

In certain embodiments, R¹ is hydrogen, hydroxy, or halogen.

In certain embodiments, R¹ is $^{18}F$.

In certain embodiments, E is triazole positioned between linking groups such as the following groups alone or in combination, ether, amine, amide, ester, carbonyl, thiol, dithiol, thiolester, aromatic, heteroaromatic, or hydrocarbon groups.

In certain embodiments, G is $^{18}F$.

In certain embodiments, the disclosure relates to compounds of formula I with formula IB

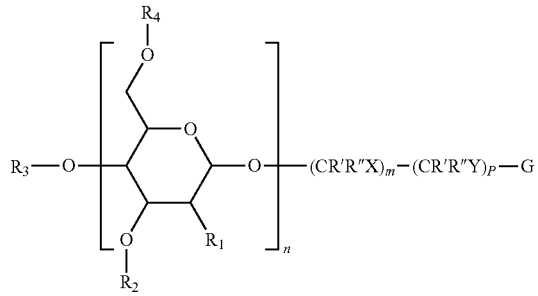

Formula IB or salts thereof wherein, n is 2, 3, 4, 5, 6, 7, 8, 9, 10, 11, 12, 13, 14, or 15;

m is 1, 2, 3, 4, 5, 6, 7, 8, 9, 10, 11, 12, 13, 14, 15, 16, 17, 18, 19, 20, 21, 22, 23, or 24;

p is 0, 1, 2, 3, 4, 5, 6, 7, 8, 9, 10, 11, 12, 13, 14, 15, 16, 17, 18, 19, 20, 21, 22, or 23;

R' and R" are at each occurrence individually and independently hydrogen, halogen, alkyl, alkoxy, or hydroxyl;

X and Y are at each occurrence individually and independently —O—, —S—, —S—S—, —NH—, —(C=O)—, —NH(C=O)—, (C=O)NH— —O(C=O)—, —(C=O)O—, —S(C=O)—, —(C=O)S—, —SO—, —SO₂—, —NHSO₂—, —SO₂NH—, —(CH₂CH₂O)$_q$—, —(CH₂)$_r$—, a disubstituted carbocyclyl, a di-substituted aryl, a di-substituted heterocyclyl, or absent;

q may be 1 to 1000;

r may be 1 to 22;

G is a radionuclide, fluorescent molecule, an antibiotic, or an azide group;

R¹, R², R³, and R⁴, are each individually and independently hydrogen, alkyl, halogen, nitro, cyano, hydroxy, amino, mercapto, formyl, carboxy, alkanoyl, carbamoyl, alkoxy, alkylthio, alkylamino, (alkyl)₂-amino, alkylsulfinyl, alkylsulfonyl, arylsulfonyl, carbocyclyl, aryl, or heterocyclyl, wherein each R¹, R², R³, and R⁴ are optionally substituted with one or more, the same or different, R⁵;

R⁵ is alkyl, halogen, nitro, cyano, hydroxy, amino, mercapto, formyl, carboxy, alkanoyl, carbamoyl, alkoxy, alkylthio, alkylamino, (alkyl)₂-amino, alkylsulfinyl, alkylsulfonyl, arylsulfonyl, carbocyclyl, aryl, or heterocyclyl, wherein R⁵ is optionally substituted with one or more, the same or different, R⁶; and R⁶ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X or Y is a di-substituted 1,2,3-triazole.

In certain embodiments, the disclosure relates to compounds of formula I with formula IC,

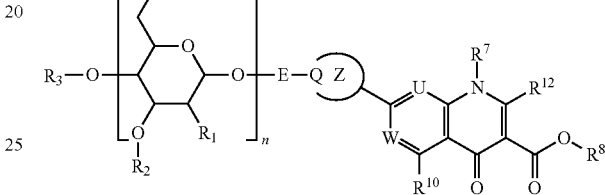

Formula IC or salts thereof wherein, n is 2, 3, 4, 5, 6, 7, 8, 9, 10, 11, 12, 13, 14, or 15;

E is a linking group;

Q is N in the ring of Z, or N is an amino or alkylamino group attached to the Z ring; or Q is O of an oxygen attached to the Z ring, wherein the Z ring may be optionally substituted with one or more, the same or different, R¹³;

U is N or CR₁₁;

W is N or CR₉;

Z is a carbocyclic or heterocyclic ring;

R¹, R², R³, and R⁴, are each individually and independently hydrogen, alkyl, halogen, nitro, cyano, hydroxy, amino, mercapto, formyl, carboxy, alkanoyl, carbamoyl, alkoxy, alkylthio, alkylamino, (alkyl)₂-amino, alkylsulfinyl, alkylsulfonyl, arylsulfonyl, carbocyclyl, aryl, or heterocyclyl, wherein each R¹, R², R³, and R⁴ are optionally substituted with one or more, the same or different, R⁵;

R⁵ is alkyl, halogen, nitro, cyano, hydroxy, amino, mercapto, formyl, carboxy, alkanoyl, carbamoyl, alkoxy, alkylthio, alkylamino, (alkyl)₂-amino, alkylsulfinyl, alkylsulfonyl, arylsulfonyl, carbocyclyl, aryl, or heterocyclyl, wherein R⁵ is optionally substituted with one or more, the same or different, R⁶;

R⁶ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R⁷ is alkyl, carbocyclyl, or aryl, wherein R⁷ is optionally substituted with one or more, the same or different R¹³; or R⁷ and R¹¹ form a heterocarbocyclic ring optionally substituted with R¹³;

R⁸ is hydrogen, alkyl or alkanoyl;
R⁹ is a hydrogen or halogen;
R¹⁰ is hydrogen, alkoxy, amino, or alkyl;
R¹¹ is hydrogen, alkoxy, or halogen; and
R¹² is hydrogen;
R¹³ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, E is —(CR'R''X)$_m$—(CR'R''Y)$_p$— wherein
m is 1, 2, 3, 4, 5, 6, 7, 8, 9, 10, 11, 12, 13, 14, 15, 16, 17, 18, 19, 20, 21, 22, 23, or 24;
p is 0, 1, 2, 3, 4, 5, 6, 7, 8, 9, 10, 11, 12, 13, 14, 15, 16, 17, 18, 19, 20, 21, 22, or 23;
R' and R'' are at each occurrence individually and independently hydrogen, alkyl, halogen, or hydroxyl;
X and Y are at each occurrence individually and independently —O—, —S—, —S—S—, —NH—, —(C=O)—, —NH(C=O)—, (C=O)NH—, —O(C=O)—, —(C=O)O—, —S(C=O)—, —(C=O)S—, —SO—, —SO$_2$—, —NHSO$_2$—, —SO$_2$NH—, —(CH$_2$CH$_2$O)$_q$—, —(CH$_2$)$_r$—, a disubstituted carbocyclyl, a di-substituted aryl, a di-substituted heterocyclyl, or absent;
q may be 1 to 1000; and
r may be 1 to 22.

In certain embodiments, the disclosure relates to compounds of formula I with formula ID, —(C=O)—, —NH(C=O)—, (C=O)NH—, —O(C=O)—, —(C=O)O—, —S(C=O)—, —(C=O)S—, —SO—, —SO$_2$—, —NHSO$_2$—, —SO$_2$NH—, —(CH$_2$CH$_2$O)$_q$—, —(CH$_2$)$_r$—, a disubstituted carbocyclyl, a di-substituted aryl, a di-substituted heterocyclyl, or absent;
q may be 1 to 1000;
r may be 1 to 22;
R¹, R², R³, and R⁴, are each individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein each R¹, R², R³, and R⁴ are optionally substituted with one or more, the same or different, R⁵;
R⁵ is alkyl, halogen, nitro, cyano, hydroxy, amino, mercapto, formyl, carboxy, alkanoyl, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein R⁵ is optionally substituted with one or more, the same or different, R⁶;
R⁶ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
R⁷ is alkyl, carbocyclyl, or aryl, wherein R⁷ is optionally substituted with one or more, the same or different R¹³; or R⁷ and R¹¹ form a heterocarbocyclic ring optionally substituted with R¹³;

Formula ID

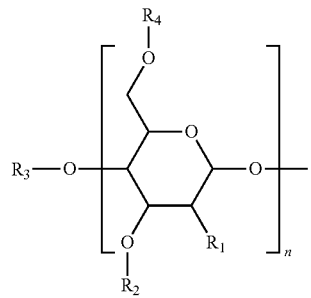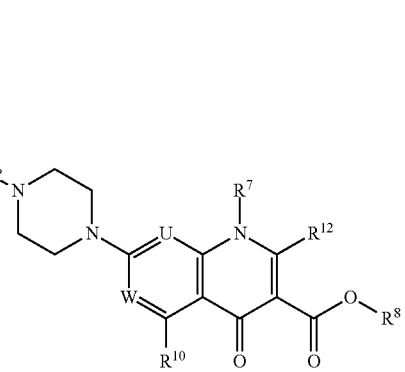

or salts thereof wherein,
U is N or CR$_{11}$;
W is N or CR$_9$;
n is 2, 3, 4, 5, 6, 7, 8, 9, 10, 11, 12, 13, 14, or 15;
m is 1, 2, 3, 4, 5, 6, 7, 8, 9, 10, 11, 12, 13, 14, 15, 16, 17, 18, 19, 20, 21, 22, 23, or 24;
p is 0, 1, 2, 3, 4, 5, 6, 7, 8, 9, 10, 11, 12, 13, 14, 15, 16, 17, 18, 19, 20, 21, 22, or 23;
R' and R'' are at each occurrence individually and independently hydrogen, alkyl, halogen, or hydroxyl;
X and Y are at each occurrence individually and independently —O—, —S—, —S—S—, —NH—, R⁸ is hydrogen, alkyl or alkanoyl;
R⁹ is a hydrogen or halogen;
R¹⁰ is hydrogen, alkoxy, amino, or alkyl;
R¹¹ is hydrogen, alkoxy, or halogen; and
R¹² is hydrogen;
R¹³ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Pharmaceutical Formulations

Within certain embodiments, the disclosure contemplates compounds and conjugates disclosed herein in pharmaceutical composition, optionally as a pharmaceutically acceptable salt, in combination with a pharmaceutically acceptable excipient. Pharmaceutical compositions of the compounds of this application, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride or sodium citrate, may also be added.

Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. Such a liquid formulation may be administered directly p.o. or filled into a soft gelatin capsule.

The pharmaceutical compositions of the application may be in the form of a sterile injectable preparation. Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

In some cases, protective groups may be introduced and finally removed. Certain "protective groups" such as an N-acetyl group, may be incorporated and remain as part of the desired compound. Suitable protective groups for amino, hydroxy and carboxy groups are described in Greene et al., Protective Groups in Organic Synthesis, Second Edition, John Wiley and Sons, New York, 1991. Standard organic chemical reactions can be achieved by using a number of different reagents, for examples, as described in Larock: Comprehensive Organic Transformations, VCH Publishers, New York, 1989.

Radio-labeling a small molecule, such as a compound of the present application, usually involves displacement of a suitably activated precursor with a radioactive moiety in a compatible reaction media. In the case of $^{18}$F-labeling, the [$^{18}$F]fluoride attachment to the precursor occurs via nucleophilic substitution of a leaving group, such as mesylate, tosylate, bromide, iodide or diazonium salt, or nitro group. Depending on the compound, the preparation of a radiolabeled compound generally consists of at least two steps. The first step involves the preparation of radio-labeling precursor, in which various functional groups have been appropriately protected and a proper leaving group has been incorporated. The second sequence then involves the radio-labeling, and removal of the protecting group as known in the art

TERMS

As used herein, "alkyl" means a noncyclic straight chain or branched, unsaturated or saturated hydrocarbon such as those containing from 1 to 10 carbon atoms, while the term "lower alkyl" or "$C_{1-4}$ alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., $-S-CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., $-NH-CH_3$).

"Alkanoyl" refers to an alkyl as defined above attached through a carbonyl bride (i.e., $-(C=O)alkyl$).

"Alkylsulfonyl" refers to an alkyl as defined above attached through a sulfonyl bridge (i.e., $-S(=O)_2$ alkyl) such as mesyl and the like, and "Arylsulfonyl" refers to an aryl attached through a sulfonyl bridge (i.e., $-S(=O)_2$ aryl).

"Alkylsulfinyl" refers to an alkyl as defined above attached through a sulfinyl bridge (i.e. $-S(=O)alkyl$).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, $-NR_aR_b$, $-NR_aC(=O)R_b$, $-NR_aC(=O)NR_aNR_b$, $-NR_aC(=O)OR_b$, $NR_aSO_2R_b$, $-C(=O)R_a$, $-C(=O)OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the term "saccharide" refers to sugars or sugar derivatives, polyhydroxylated aldehydes and ketones with an empirical formula that approximates $C_m(H_2O)_n$, i.e., wherein in and n are the same or about the same. Contemplated saccharides include, e.g., malotose, isomalose, and lactose with an empirical formula of $C_2H_{22}O_{11}$. The term is intended to encompass sugar monomers, oligomers, and polymers. The terms oligosaccharide and polysaccharide are used interchangeably, and these saccharides typically contain between two and ten monosaccharide units, or greater than ten monosaccharide units. In certain embodiments of the disclosure, the saccharide is a dextrin, maltodextrin, or cyclodextrin. Dextrins are mixtures of polymers of D-glucose units linked by α-(1→4) or α-(1→6) glycosidic bonds. Maltodextrin consists of D-glucose units connected in chains of variable length. The glucose units are primarily linked with α(1→4) glycosidic bonds. Maltodextrin is typically composed of a mixture of chains that vary from three to nineteen glucose units long. Maltose is a disaccharide formed from two units of glucose joined with an α(1→4) bond. Isomaltose has two glucose molecules linked through an α(1→6) bond. In certain embodiments, the disclosure contemplates cyclic and non-cyclic polysaccharides. Typical cyclodextrins contain a number of glucose monomers ranging from six to eight units in a ring, such as alpha cyclodextrin; a six membered sugar ring molecule; beta cyclodextrin, a seven sugar ring molecule; and gama cyclodextrin, an eight sugar ring molecule.

As used herein, the term "conjugate" or "conjugated," and the like refer to molecular entities being linked together through covalent bonds. Conjugation may be accomplished by directly coupling the two molecular entities, e.g., creating an ester or amide from an hydroxyl group, amino group, and a carboxylic acid. Conjugation may be accomplished by indirectly coupling the two molecular entities, e.g., instituting a linking group such as a polyethylene glycol. Conjugation may be accomplished by modifying the molecular entities with chemical groups that react with one another, e.g., alkyne-functionalized entity with an azide-functionalized entity or the reduction of thiol groups on individual entities to form a disulfide bond.

"Positron emission tomography (PET) refers to an imaging technique that produces a three-dimensional image by detecting pairs of gamma rays emitted indirectly by a positron-emitting radionuclide tracer. Three-dimensional images of tracer concentration within the area are then constructed by computer analysis. A radioactive tracer is administered to a subject e.g., into blood circulation. Typically there is a waiting period while tracer becomes concentrated in areas of interest; then the subject is placed in the imaging scanner. As the radioisotope undergoes positron emission decay, it emits a positron, an antiparticle of the electron with opposite charge, until it decelerates to a point where it can interact with an electron, producing a pair of (gamma) photons moving in approximately opposite directions. These are detected in the scanning device. The technique typically utilizes simultaneous or coincident detection of the pair of photons moving in approximately opposite direction (the scanner typically has a built-in slight direction-error tolerance). Photons that do not arrive in pairs (i.e. within a timing-window) are typically ignored. One typically localizes the source of the photons along a straight line of coincidence (also called the line of response, or LOR). This data is used to generate an image.

The term "radionuclide" or "radioactive isotope" refers to isotopes exhibiting radioactive decay (i.e., emitting positrons) and radiolabeling agents comprising a radioactive isotope (e.g., [$^{11}$C]methane, [$^{11}$C]carbon monoxide, [$^{11}$C] carbon dioxide, [$^{11}$C]phosgene, [$^{11}$C]urea, [$^{11}$C]cyanogen bromide, as well as various acid chlorides, carboxylic acids, alcohols, aldehydes and ketones containing carbon-11). Such isotopes are also referred to in the art as radioisotopes or radionuclides. Radioactive isotopes are named herein using various commonly used combinations of the name or symbol of the element and its mass number (e.g., $^{18}$F, F-18, or fluorine-18). Exemplary radioactive isotopes include I-124, F-18 fluoride, C-11, N-13, and O-15, which have half-lives of 4.2 days, 110 minutes, 20 minutes, 10 minutes and 2 minutes, respectively. The radioactive isotope is preferably dissolved in an organic solvent, such as a polar aprotic solvent. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and Tl-201. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

Other methods of preparing radiolabeled ligands are well known in the art. Example of such methods are disclosed in, for example: 1) Jewett, D. M. (1992) A Simple Synthesis of [$^{11}$C]Methyl Triflate Appl. Radiat. Isot. 43, 1383-1385; 2) Crouzel, C. Langstrom, B., Pike, V. W., and Coenen, H. H. (1987) Recommendations for a practical production of [$^{11}$C] methyl iodide Appl. Radiat. Isot. Int. J. Appl. Instrum. Part A 38, 601-603; Dannals, R. F., Ravert, H. T.; 3) Wilson, A. A. (1990) Radiochemistry of Tracers for Neurotransmitter Receptor Studies. In: Quantitative Imaging Neuroreceptors, Neurotransmitters, and Enzymes. (Edited by Frost), J. J. Wagner Jr., H. N. pp. 19-35, Raven Press, New York; 4) Jewett, D. M., Manger, T. J., and Watkins, G. L. (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York; 5) Marazano, C., Maziere, M., Berger, G., and Comar, D. (1977) Synthesis of methyl iodide-.sup.11C and formaldehyde-$^{11}$C. Appl. Radiat. Isot. 28, 49-52; 6) Watkins, G., Jewett, D., Mulholland, G., Kitbourn, M., and Toorongian, S. (1988) A Captive Solvent Method for Rapid N—[$^{11}$C] Methylation of Secondary Amides Application to the Benzodiazepine, 4'-Chlorodiazepam (RO5-4864) Appl. Radiat. Isot. 39, 441→444; and 7) Wilson, A. A., DaSilva, J. N., and Houle, S. (1996) In vivo evaluation of [$^{11}$C] and [$^{5}$F]-labeled cocaine analogues as potential dopamine transporter ligands for positron emission tomography Nucl. Med. Biol. 23, 141-146. The subject matter of all references cited herein are incorporated herein by reference in their entirety.

EXAMPLES

Example 1

Synthesis of MDP-1 and MDP-2

See FIG. 2. MDP-1 and MDP-2 were synthesized by conjugating alkyne-functionalized fluorescent dyes 2 and 3 to azide-functionalized maltohexaose 1, using the click reaction. The details of the click reaction between 1 and 3 used to generate MDP-2 are described below. The compounds 1 (57.0 mg, 0.03 mmol) and 3 (39.0 mg, 0.06 mmol) were dissolved in DMF (5 ml), to which was added CuI (0.6 mg, 3.0 µmol) and DIPEA (1.2 mg, 0.01 mmol). The mixture was stirred at room temperature for 24 h under nitrogen and the solvent was removed in vacuo. The residue was redissolved in $CH_2Cl_2$ (20 ml) and washed with water (5 ml) and brine (5 ml). The organic phase was dried over $Na_2SO_4$, filtered and evaporated to dryness in vacuo. The residue was purified by flash column chromatography on silica gel ($CH_2Cl_2/CH_3OH$, 15/1) to afford the intermediate 15 in a 73% yield (55.0 mg). This intermediate 15 (50.0 mg, 0.02 mmol) was deprotected in a mixture of $CH_3OH$ (2 ml) and aqueous LiOH (1.0 M, 2 ml) for 24 h under nitrogen. The crude MDP-2 was isolated by neutralizing the reaction mixture with Dowex 50W resin, filtering, and concentrating in vacuo. MDP-2 was purified by flash column chromatography on silica gel ($CH_2Cl_2/CH_3OH/H_2O$, 5/5/2) (33.8 mg, quantitative).

Figure 6:
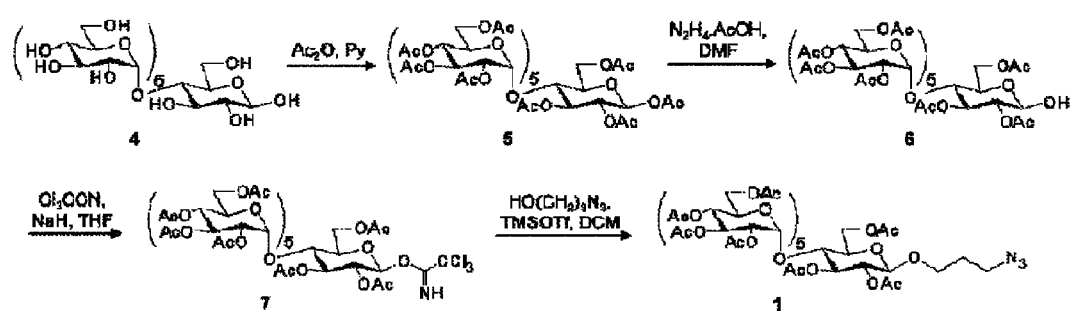
FIG. 6 schematically illustrates the synthesis of azide functionalized maltohexaose.

Synthesis of azide functionalized maltohexaoside (1). See FIG. 6. Synthesis of α-D-Glucopyranose,2,3,4,6-tetra-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)-1,2,3,6-tetraacetate (5). To a stirred solution of Maltohexaose 4 (0.5 g, 0.51 mmol) in pyridine (10 mL) was added $Ac_2O$ (5 mL). The reaction mixture was stirred at room temperature for 18 hours under nitrogen and then concentrated in vacuo. The residue was dissolved in EtOAc (100 mL) and washed with aqueous $Na_2CO_3$ (1M, 10 mL×3), aqueous HCl (0.1M, 10 mL), and brine (10 mL×2). The organic layer was dried over $Na_2SO_4$, filtered and evaporated to dryness in vacuo. The residue was purified by flash column chromatography on silica gel (hexane/EtOAc, 2:3) to afford 5 (0.85 g, 90.1%). $^1$H NMR ($CDCl_3$, 400 MHz): δ (ppm) 6.18 (d, 0.5H, J=3.2 Hz, α1-H), 5.66 (d, 0.5H, J=8.0 Hz, β1-H), 5.43 (t, 1H, J=10.0 Hz, 3-H), 5.34-5.22 (m, 10H, 3-H), 5.00 (t, 1H, J=10.0 Hz, 4-H), 4.88 (dd, 0.5H, J=3.7 and 10.0 Hz, α 2-H), 4.77 (dd, 1H, J=3.9 and 10.5 Hz, 2-H), 4.67-4.63 (m, 4H, 2-H), 4.43-4.40 (m, 4H), 4.22-3.81 (m, 21H), 2.16, 2.15, 2.13, 2.11, 2.10, 2.09, 2.08, 2.06, 2.02, 1.99, 1.97, 1.95, 1.93, 1.91, 1.88 (60H, 15 s, $CH_3$). $^{13}$C NMR ($CDCl_3$, 100 MHz): δ (ppm) 170.9, 170.8, 170.7, 170.6, 170.5, 170.3, 170.2, 170.1, 170.0, 169.9, 169.8, 169.7, 169.6, 169.2, 168.9 (C=O), 96.1 (1-C), 96.0 (1-C), 95.9 (1-C), 95.8 (1-C), 95.7 (1-C), 91.4, 89.0, 77.6, 77.5, 77.3, 75.3, 73.6, 73.5, 73.4, 73.1, 72.5, 72.4, 71.9, 71.8, 71.7, 71.6, 71.1, 70.7, 70.6, 70.3, 70.2, 69.9, 69.5, 69.2, 69.1, 68.6, 68.0, 62.8, 62.7, 62.6, 62.5, 62.4, 62.3, 61.5, 29.8, 21.2, 21.1, 21.0, 20.9, 20.8, 20.7, 20.6, 20.5, 20.3. HRMS (MALDI) m/z Found: 1853.5298, calculated: 1853.5280 for $C_{76}H_{102}NaO_{51}$ $[M+Na]_+$.

Synthesis of α-D-Glucopyranose,2,3,4,6-tetra-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)-2,3,6-triacetate (6). To a stirred solution of 5 (0.73 g, 0.4 mmol) in DMF (10 mL) was added $N_2H_4$.HOAc (46.0 mg, 0.5 mmol). The reaction mixture was heated to 60° C. for 12 hours under nitrogen, and the mixture was concentrated in vacuo. The residue was dissolved in EtOAc (100 mL) and washed with water (30 mL×2) and brine (10 mL). The organic phase was dried over $Na_2SO_4$, filtered and evaporated to dryness in vacuo. The residue was purified by flash column chromatography on silica gel (hexane/EtOAc, 1:3) to afford 6 (0.66 g, 93.1%). $^1$H NMR ($CDCl_3$, 400 MHz): δ (ppm) 5.56 (t, 1H, J=9.6 Hz, 3-H), 5.42-5.25 (m, 10H), 5.06 (t, 1H, J=9.2 Hz, 4-H), 4.83 (dd, 1H, J=4.0 and 9.6 Hz, α 2-H), 4.78-4.69 (m, 5H), 4.54-4.45 (m, 4H), 4.33-3.58 (m, 21H), 2.18-1.96 (s, 57H, $CH_3$). $^{13}$CNMR (100 MHz, $CDCl_3$): δ (ppm) 171.0, 170.9, 170.8, 170.7, 170.6, 170.4, 170.1, 170.0, 169.9, 169.8, 169.7, 169.6 (C=O), 95.9 (1-C), 95.8 (1-C), 90.2 (1-C), 77.6, 73.9, 73.5, 72.6, 72.5, 71.9, 71.8, 70.6, 70.2, 69.7, 69.1, 68.6, 68.1, 67.9, 63.1, 62.6, 62.5, 62.3, 61.6, 60.6, 21.2, 21.1, 21.0, 21.0, 20.9, 20.8, 20.7. HRMS (MALDI) m/z Found: 1811.5197, calculated: 1811.5175 for $C_{74}H_{100}NaO_{50}$ $[M+Na]^+$.

Synthesis of α-D-Glucopyranose,2,3,4,6-tetra-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)-2,3,6-triacetate 1-(2,2,2-trichloroethanimidate) (7). To a stirred solution of 6 (0.53 g, 0.3 mmol) in dry THF (10 mL) was added trichloroacetonitrile (60 μL, 0.6 mmol), and the solution was cooled to 0° C. NaH (9.0 mg, 0.4 mmol) was then added and the suspension was stirred at 0° C. for 6 hours under nitrogen. The reaction mixture was concentrated in vacuo to afford crude 7 (0.58 g, quantitative). The crude compound was used for the next step without purification. $^1$H NMR (400 MHz, $CDCl_3$): δ (ppm) 8.58 (s, 1H, NH), 6.50 (d, J=3.6 Hz, 1H, H-1), 5.60 (t, 1H, J=9.6 Hz, 3-H), 5.43-5.28 (m, 10H), 5.11 (t, 1H, J=9.2 Hz, 4-H), 4.87-4.73 (m, 6H), 4.56-3.60 (m, 25H), 2.18-1.96 (s, 57H, $CH_3$).

Synthesis of β-D-Glucopyranose,2,3,4,6-tetra-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)-2,3,6-triacetate 1-(3'-azidopropyl) (1). To a stirred solution of crude 7 (0.38 g, 0.2 mmol) and 3-azidopropanol (0.1 g, 1.0 mmol) in dry $CH_2Cl_2$ (10 mL) was added 4 Å M.S. The mixture was stirred under nitrogen at 0° C. for 1 hour. TMSOTf (45 μL, 0.25 mmol) was then added and the mixture was stirred at 0° C. for 1 hour. The mixture was allowed to warm to room temperature After 1 hour the reaction was quenched with $Et_3N$ and concentrated in vacuo. The residue was dissolved in EtOAc (50 mL) and washed with water (10 mL×2) and brine (10 mL). The organic phase was dried over $Na_2SO_4$, filtered and evaporated to dryness in vacuo. The residue was purified by flash column chromatography on silica gel (hexane/EtOAc, 1:2) to afford 1 (0.15 g, 39.3%). $^1$H NMR (400 MHz, $CDCl_3$): δ (ppm) 5.41-5.22 (m, 11H), 5.06 (t, 1H, J=10.0 Hz, 4-H), 4.82 (dd, 1H, J=4.0 and 10.0 Hz, α 2-H), 4.77-4.70 (m, 3H), 4.52-4.48 (m, 6H), 4.37-3.88 (m, 20H), 3.68-3.55 (m, 2H, N3CH2CH2CH2O), 3.36 (t, 2H, J=6.4 Hz, N3CH2CH2CH2O), 2.24-1.93 (s, 57H, $CH_3$), 1.83 (m, 2H, N3CH2CH2CH2O). $^{13}$CNMR (100 MHz, $CDCl_3$): δ (ppm) 170.9, 170.9, 170.9, 170.8, 170.7, 170.6, 170.6, 170.5, 170.3, 170.0, 169.9, 169.9, 169.8, 169.7, 169.7, 169.6 (C=O), 100.5 (β 1-C), 95.9 (1-C), 95.8 (1-C), 90.2 (1-C), 77.6, 75.5, 73.9, 73.6, 73.4, 73.3, 72.5, 72.4, 72.3, 71.9, 71.8, 71.7, 70.7, 70.6, 70.2, 69.5, 69.1, 68.6, 68.1, 66.6, 63.0, 62.7, 62.6, 62.5, 62.3, 61.6, 48.2, 29.1, 21.1, 21.1, 21.0, 21.0, 20.9, 20.8, 20.8, 20.7. HRMS (MALDI) m/z Found: 1894.5679, calculated: 1894.5658 for $C_{77}H_{105}N_3NaO_{50}$ $[M+Na]^+$.

Figure 7:
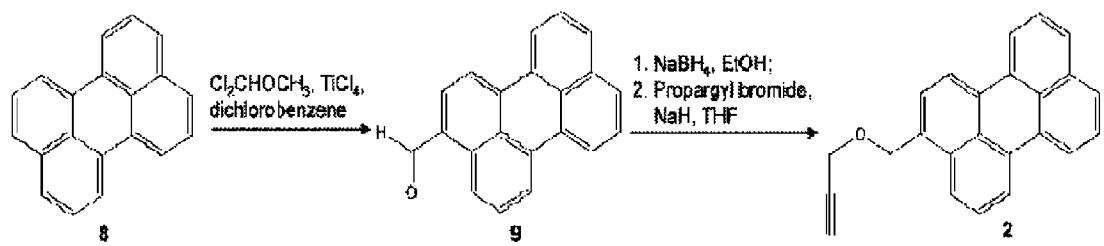
FIG. 7 schematically illustrates the synthesis of alkyne functionalized perylene.

Synthesis of alkyne functionalized perylene (2). See FIG. 7. Synthesis of formylperylene (9) To a stirred solution of perylene 8 (1.0 g, 4.0 mmol) in 1,2-dichlorobenzene (25 mL) was added 1,1-dichloromethyl methyl ether (0.68 g, 6.0 mmol) and $TiCl_4$ (1.1 g, 6.0 mmol). The reaction mixture was stirred at 0° C. for 1 hour under nitrogen, and then allowed to warm to room temperature. The reaction mixture was diluted with $CH_2Cl_2$ (100 mL) and acidified with aqueous HCl (0.1M, 10 mL). The mixture was washed with water (50 mL×3) and brine (20 mL). The organic phase was dried over $Na_2SO_4$, filtered and evaporated to dryness in vacuo. The residue was purified by flash column chromatography on silica gel (hexane/EtOAc, 15:1) to afford 9 (0.81 g, 72.3%). $^1$H NMR ($CDCl_3$, 400 MHz): δ (ppm) 10.31 (s, 1H, CHO); 9.11 (d, 1H, J=8.8 Hz, aromatic); 8.26-8.15 (m, 4H, aromatic); 7.85 (d, 1H, J=8.0 Hz, aromatic); 7.78 (d, 1H, J=8.0 Hz, aromatic); 7.71 (d, 1H, J=8.0 Hz, aromatic); 7.65 (m, 1H, aromatic); 7.48 (m, 2H, aromatic). $^{13}$C NMR ($CDCl_3$, 100 MHz): δ (ppm) 193.3, 137.1, 136.6, 133.8, 131.4, 130.6, 130.0, 129.7, 129.4, 129.3, 129.0, 128.6, 127.9, 127.2, 127.1, 126.9, 123.8, 123.4, 122.0, 121.3, 119.8. HRMS (MALDI) m/z Found: 317.0960, calculated: 317.0937 for $C_{22}H_{14}NaO$ $[M+Na]^+$.

Synthesis of (Perylenyl-3-methyl)propargyl ether (2). To a stirred solution of 9 (0.56 g, 2.0 mmol) in ethanol (20 mL) was added $NaBH_4$ (0.11 g, 3.0 mmol). The reaction mixture was stirred at room temperature for 30 minutes under nitrogen, and then quenched with aq $NH_4Cl$ (0.1M, 5 mL). The solution was diluted with EtOAc (50 mL) and the organic phase was washed with water (10 mL×2) and saturated $NaHCO_3$ (10 mL). The organic phase was dried over $Na_2SO_4$, filtered and evaporated to dryness in vacuo. The residue was dissolved in THF (20 mL), to which was added NaH (16 mg, 4.0 mmol) under vigorous stirring. The mixture was stirred at room temperature for 10 minutes under nitrogen, and 80% propargyl bromide in toluene (0.63 g, 4.0 mmol) was added. The reaction was kept at room temperature for 2 hours, and the solvent was removed in vacuo. The residue was dissolved in EtOAc (30 mL) and washed with water (10 mL×2) and brine (10 mL). The organic phase was dried over $Na_2SO_4$, filtered and evaporated to dryness in vacuo. The residue was purified by flash column chromatography on silica gel (hexane/EtOAc, 5:1) to afford 2 (0.55 g, 85.9%). $^1$H NMR ($CDCl_3$, 400 MHz): δ (ppm) 8.41-8.27 (m, 4H, aromatic); 7.96 (d, 1H, J=8.0 Hz, aromatics); 7.81 (d, 2H, J=8.0 Hz, aromatic); 7.62 (m, 1H, aromatics); 7.56 (m, 3H, aromatics); 4.93 (s, 2H, ArCH2); 4.31 (d, 2H, J=2.3 Hz, CH2C); 3.54 (t, 1H, J=2.3 Hz, CH). $^{13}$C NMR ($CDCl_3$, 100 MHz): δ (ppm) 134.1, 133.2, 132.5, 130.7, 130.1, 130.2, 127.9, 127.8, 127.8, 127.5, 127.3, 127.1 126.8, 124.0, 120.8, 120.7, 120.5, 120.2, 80.0, 77.5, 69.1, 57.1. HRMS (MALDI) m/z Found: 343.1113, calculated: 343.1093 for $C_{24}H_{16}NaO$ [M+Na]$^+$.

Figure 8:
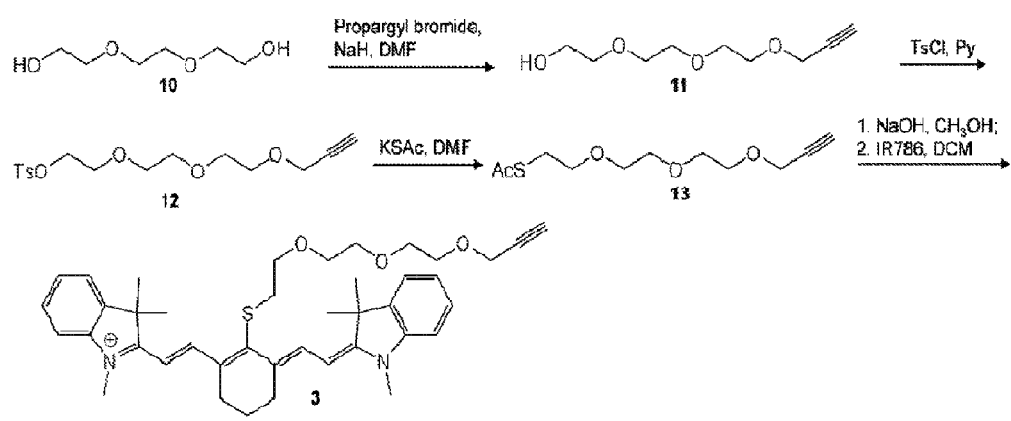
FIG. 8 schematically illustrates the synthesis of alkyne functionalized IR786.

Synthesis of 2-(2-(2-(Prop-2-ynyloxy)ethoxy)ethoxy) ethanol (11). See FIG. 8. To a stirred solution of triethylene glycol 10 (2.2 mL, 16.7 mmol) in THF was added sodium hydride (0.24 g, 6.0 mmol). The mixture was stirred at room temperature for 1 hour under nitrogen after which propargyl bromide (0.6 mL, 6.0 mmol) was added. The mixture was stirred at room temperature overnight, diluted with water (10 mL) and then neutralized with 0.1M HCl (15 mL). The resulting mixture was extracted with EtOAc (100 mL×3) and the extract was washed with brine (100 mL). The organic phase was dried over $Na_2SO_4$, filtered and evaporated to dryness in vacuo. The residue was purified by flash column chromatography on silica gel (hexanes/EtOAc, 1:1) to afford 11 as a colorless oil (0.46 g, 41.3%). $^1$H NMR (400 MHz, $CDCl_3$): δ (ppm) 4.25 (d, 2H, J=2.4 Hz, CHCCH2O), 3.68-3.63 (m, 11H, OCH2 and OH) 3.59 (t, 2H, J=4.4 Hz, CH2OH), 2.41 (t, 1H, J=2.4 Hz, CHCCH2). $^{13}$C NMR (100 MHz, $CDCl_3$): δ (ppm) 79.3, 74.5, 72.1, 70.5, 70.3, 70.1, 69.0, 61.5, 58.2. HRMS (MALDI) m/z Found: 211.0959, calculated: 211.0941 for $C_9H_{16}NaO_4$ [M+Na]$^+$.

Synthesis of 2-(2-(2-(Prop-2-ynyloxy)ethoxy)ethoxy) ethyl 4-methylbenzenesulfonate (12). To a stirred solution of 11 (0.37 g, 2.0 mmol) in pyridine (10 mL) was added 4-toluenesulfonyl chloride (0.80 g, 4.0 mmol). The mixture was stirred vigorously at room temperature for 6 hours under nitrogen. The mixture was then poured into ice water and extracted with $CH_2Cl_2$ (50 mL×3). The combined organic phase was washed with brine, dried over $Na_2SO_4$, filtered and evaporated to dryness in vacuo. The residue was purified by flash column chromatography on silica gel (hexanes/ EtOAc, 2:1) to afford 12 as white crystals (0.65 g, 93.7%). $^1$H NMR (400 MHz, $CDCl_3$): δ (ppm) 7.83 (d, 2H, J=8.0 Hz, ArH), 7.36 (d, 2H, J=8.0 Hz, ArH), 4.21 (d, 2H, J=2.4 Hz, CHCCH2O), 4.17 (t, 2H, J=4.8 Hz, CH2OTs), 3.73-3.69 (m, 4H, OCH2), 3.67-3.62 (m, 2H, OCH2), 3.60 (s, 4H, OCH2), 2.49 (s, 3H, ArCH3), 2.45 (t, 1H, J=2.4 Hz, CHCCH2). $^{13}$C NMR (100 MHz, $CDCl_3$): δ (ppm) 145.0, 133.1, 130.0, 128.3, 79.8, 74.5, 70.8, 70.7, 70.6, 70.0, 69.3, 68.7, 58.6, 21.5. HRMS (MALDI) m/z Found: 365.1043, calculated: 365.1029 for $C_{16}H_{22}NaO_6S$ [M+Na]$^+$.

Synthesis of 2-(2-(2-(prop-2-yn-1-yloxy)ethoxy)ethoxy) ethyl ethanethioate (13). To a stirred solution of 12 (340 mg, 1.0 mmol) in DMF (10 mL) was added KSAc (220 mg, 2.0 nmol). The mixture was then stirred at 60° C. for 12 hours under nitrogen and the DMF was removed under vacuum. The residue was dissolved in EtOAc (50 mL) and washed with water (10 mL×2) and brine (10 mL×2). The organic phase was dried over $Na_2SO_4$, filtered and evaporated to dryness in vacuo. The obtained residue was purified by flash column chromatography on silica gel (hexane/EtOAc, 3:1) to afford 13 (160 mg, 67.1%). $^1$H NMR (400 MHz, $CDCl_3$) δ (ppm) 4.10 (d, 2H, J=2.0 Hz, OCH2CCH), 3.59-3.51 (m, 8H, OCH2), 3.49 (t, 2H, J=6.4 Hz, CH2O), 2.98 (t, 2H, J=6.4 Hz, CH2S), 2.38 (t, 1H, J=2.0 Hz, CCH), 2.23 (s, 3H, Ac). $^{13}$C NMR (100 MHz, $CDCl_3$): δ (ppm) 195.3, 79.6, 74.5, 70.4, 70.3, 70.1, 69.6, 68.9, 58.2, 30.4, 28.7. HRMS (MALDI) m/z Found: 269.0833, calculated: 269.0818 for $C_{11}H_{18}O_4S$ [M]$^+$.

Synthesis of 1,3,3-trimethyl-2-(-2-(-2-((2-(2-(2-(prop-2-yn-1-oxy)ethoxy)ethoxy)ethyl)thio)-3-(-2-(1,3,3-trimethyl-indolin-2-ylidene)ethylidene)cyclohex-1-en-1-yl)vinyl)-3H-indol-1-ium (3). To a stirred solution of 13 (120 mg, 0.5 mmol) in $CH_3OH$ (5 mL) was added NaOH (40 mg 1.0 mmol). The mixture was stirred at room temperature for 2 hours under nitrogen and the solvent was removed in vacuo. The residue thus obtained was dissolved in $CH_2Cl_2$ (10 mL) and mixed with a 10 mL $CH_2Cl_2$ solution of IR786 perchlorate (290 mg, 0.5 mmol). The reaction mixture was stirred at room temperature overnight under nitrogen, and diluted with $CH_2Cl_2$ (20 mL). The mixture was washed with water (10 mL×2) and brine (10 mL). The organic phase was dried over $Na_2SO_4$, filtered and evaporated to dryness in vacuo. The residue was purified by flash chromatography on silica gel ($CH_2Cl_2/CH_3OH$, 20:1) to afford 3 as a solid (250 mg, 76.8%). $^1$H NMR (400 MHz, $CDCl_3$): δ (ppm) 8.77 (d, 2H, J=14.0 Hz, ArH), 7.37-7.26 (m, 4H, ArH), 7.21-7.14 (m, 4H, ArH), 6.15 (d, 2H, J=14.0 Hz, ArH), 4.11 (d, 2H, J=1.2 Hz, OCH2-C), 3.68 (s, 6H, NCH3), 3.63-3.55 (m, 12H, OCH2CH2O), 2.93 (d, 2H, J=6.8 Hz, SCH2), 2.62 (t, 4H, J=6.0 Hz, C=CCH2), 2.36 (t, 1H, J=1.2 Hz, Alkyne), 1.88 (m, 2H, CH2CH2CH2), 1.69 (s, 12H, CCH3). $^{13}$C NMR (100 MHz, $CDCl_3$): δ (ppm) 172.6, 158.5, 145.8, 142.8, 140.7, 134.1, 128.7, 125.1, 122.1, 110.6, 101.4, 74.6, 70.5, 70.3, 70.2, 69.0, 58.3, 49.0, 32.4, 27.9, 26.5. HRMS (MALDI) m/z Found: 651.3635, calculated: 651.3615 for $C_{41}H_{51}N_2NaO_3S$ [M+Na]$^+$.

Figure 9:
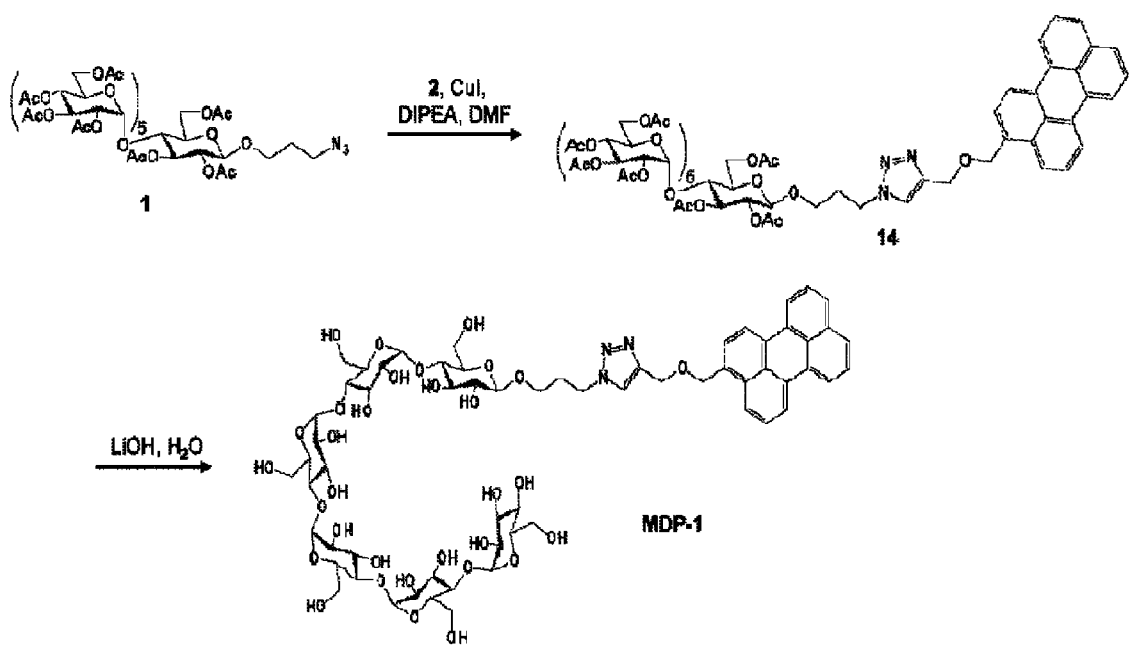
FIG. 9 schematically illustrates the synthesis of MDP-1.

Synthesis of MDP-1 Synthesis of β-D-Glucopyranose,-2, 3,4,6-tetra-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)-2,3,6-triacetate 1-(3'-triazolepropyl perylene) (14). See FIG. 9. To a stirred solution of 1 (38.0 mg, 0.02 mmol) and 2 (13.0 mg, 0.04 mmol) in DMF (5 mL) was added CuI (0.2 mg, 1.0 μmol) and DIPEA (1.2 mg, 0.01 mmol). The mixture was stirred at room temperature for 12 hours under nitrogen and the solvent was removed in vacuo. The residue was dissolved in $CH_2Cl_2$ (20 mL) and washed with water (5 mL×2) and brine (5 mL). The organic phase was dried over $Na_2SO_4$, filtered and evaporated to dryness in vacuo. The residue was purified by flash column chromatography on silica gel ($CH_2Cl_2/CH_3OH$, 15/1) to afford 14 (35.0 mg, 79.5%). $^1$H NMR (400 MHz, $CDCl_3$): δ (ppm) 8.21-8.14 (m, 4H, Aromatic), 8.09 (d, 1H, J=8.8 Hz, Aromatic), 7.90 (d, 1H, J=8.8 Hz, Aromatic), 7.66 (m, 2H, Aromatic), 7.56-7.43 (m, 4H, Aromatic), 5.43-5.26 (m, 11H), 5.03 (t, 1H, J=9.6 Hz, 4"-H), 4.97 (m, 2H, ArCH2O), 4.79 (dd, 1H, J=4.0 and 9.6 Hz, α 2'-H), 4.73 (s, 2H, CH2-C≡C), 4.72-4.68 (m, 3H), 4.52-3.91 (m, 26H), 3.75-3.52 (m, 2H, NCH2CH2CH2O), 3.38 (m, NCH2CH2CH2O), 2.22-1.96 (s, 57H, CH3), 1.85 (m, 2H, NCH2CH2CH2O). $^{13}$C NMR (100 MHz, $CDCl_3$): δ (ppm) 170.6, 170.5, 170.4, 170.3, 170.2, 170.0, 169.8, 169.7, 169.6, 169.5, 169.5, 169.4 (C=O), 145.2, 134.6, 133.1, 132.9, 131.5, 131.1, 130.9, 128.9, 128.3, 127.9, 127.8, 127.5, 126.8, 126.6, 126.5, 123.9, 123.8, 123.0, 122.8, 120.4, 120.3, 119.5, 100.2 (β 1-C), 95.9 (1-C), 95.7 (1-C), 95.6 (1-C), 76.5, 75.2, 73.8, 73.5, 73.3, 73.2, 72.6, 72.3, 72.1, 71.6, 71.6, 71.5, 71.2, 71.1, 70.5, 70.4, 70.0, 69.5, 69.3, 68.9, 68.4, 67.8, 67.7, 65.8, 64.7, 63.7, 62.9, 62.5, 62.3, 62.2, 62.1, 61.3, 53.7, 46.8, 31.7, 29.9, 29.2, 21.0, 20.8, 21.8, 21.6, 20.5. HRMS (MALDI) m/z Found: 2214.6877, calculated: 2214.6859 for $C_{101}H_{121}N_3NaO_{51}$ [M+Na]+.

Synthesis of MDP-1 To a stirred solution of 14 (32.0 mg, 0.015 mmol) in $CH_3OH$ (2 mL) was added aqueous LiOH (1.0 M, 2 mL) under nitrogen, and the reaction mixture was stirred at room temperature for 24 hours. The mixture was then neutralized with Dowex 50W resin, filtered and concentrated in vacuo. The residue was purified by flash column chromatography on silica gel ($CH_2Cl_2/CH_3OH/H_2O$, 5/5/2) to afford MDP-1 (20.8 mg, quantitative). $^1$H-NMR (400 MHz, $D_2O$): δ (ppm) 7.88-7.74, (m, 3H, Aromatic), 7.70 (d, 1H, J=8.0 Hz, ArH), 7.50 (d, 1H, J=8.0 Hz, ArH), 7.43 (s, 1H, triazole), 7.23 (d, 2H, J=8.0 Hz, ArH),7.10-7.01 (m, 4H, ArH), 5.42-5.39 (m, 5H), 4.65 (m, 2H, ArCH2O), 4.51 (s, 2H, CH2-C≡C), 4.46 (d, 1H, J=8.4 Hz, 1'-H'), 4.32 (t, J=6.8 Hz, 2H), 4.19-4.10 (m, 3H), 4.05-3.45 (m, 45H), 3.41 (m, 1H), 3.35 (m, 1H), 2.23-1.85 (m, 4H). $^{13}$C NMR (100 MHz, $D_2O$): δ (ppm) 143.2, 134.6, 133.0, 132.5, 131.7, 131.5, 130.9, 128.8, 128.3, 127.8, 127.6, 126.7, 126.5, 126.0, 123.9, 123.6, 120.3, 120.3, 120.2, 119.4, 103.5 (β 1-C), 101.1 (1-C), 100.7 (1-C), 100.2 (1-C), 77.9, 77.8, 75.5, 74.1, 73.7, 73.6, 72.7, 72.3, 72.3, 71.9, 70.0, 70.2, 68.3, 67.2, 62.7, 62.5, 62.2, 62.1, 61.8, 61.9, 58.6, 47.9, 32.4, 30.0, 28.7. HRMS (MALDI) m/z Found: 1416.4868, calculated: 1416.4852 for $C_{63}H_{83}N3NaO_{32}$ [M+Na]+.

Figure 10:
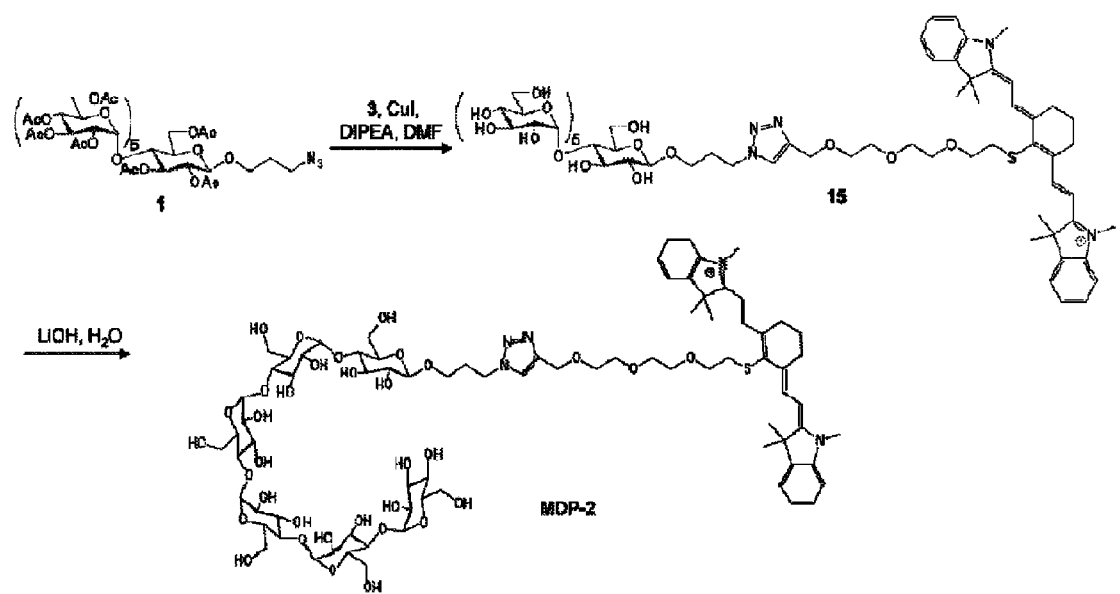
FIG. 10 schematically illustrates the synthesis of MDP-2.

Synthesis of MDP-2 Synthesis of β-D-Glucopyranose, 2,3,4,6-tetra-O-acetyl-α-D-glucopyranosyl-(1→4)—O-2,3, 6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)—O-2,3,6-tri-O-acetyl-α-D-glucopyranosyl-(1→4)-2,3,6-triacetate 1-(3'-triazolepropyl IR786) (15). See FIG. 10. To a stirred solution of 1 (57.0 mg, 0.03 mmol) and 3 (39.0 mg, 0.06 mmol) in DMF (5 mL) was added CuI (0.3 mg, 1.5 μmol) and DIPEA (1.2 mg, 0.01 mmol). The mixture was stirred at room temperature for 12 hours under nitrogen and the solvent was removed in vacuo. The residue was dissolved in $CH_2Cl_2$ (20 mL) and washed with water (5 mL×2) and brine (5 mL). The organic phase was dried over $Na_2SO_4$, filtered and evaporated to dryness in vacuo. The residue was purified by flash column chromatography on silica gel ($CH_2Cl_2/CH_3OH$, 15/1) to afford 15 (55.0 mg, 73.1%). $^1$H NMR (400 MHz, $CDCl_3$): δ (ppm) 8.78 (d, 2H, J=14.0 Hz, ArH), 7.36-7.32 (m, 4H, ArH), 7.21-6.97 (m, 5H, ArH), 6.13 (d, 2H, J=14.0 Hz, ArH), 5.38-5.21 (m, 11H), 5.03 (t, 1H, J=10.0 Hz, 4''-H), 4.81 (dd, 1H, J=4.0 and 10.0 Hz, α 2'-H), 4.71→4.68 (m, 3H), 4.47-3.52 (m, 60H), 2.93 (d, 2H, J=6.8 Hz, SCH2), 2.59 (m, 4, C≡CCH2), 2.16-1.86 (m, 61H), 1.69 (s, 12H, CCH3). $^{13}$C NMR (100 MHz, $CDCl_3$): δ (ppm) 172.6, 170.6, 170.6, 170.5, 170.4, 170.3, 170.0, 169.8, 169.7, 169.6, 169.5, 169.4, 169.4 (C=O), 157.3, 154.1, 145.8, 142.8, 142.4, 140.7, 134.1, 128.7, 127.7, 127.6, 125.0, 122.1, 114.7, 110.4, 101.3, 100.2, (β 1-C), 95.8 (1-C), 95.7 (1-C), 95.6 (1-C), 76.7, 75.2, 73.7, 73.2, 72.4, 72.3, 72.1, 71.7, 71.6, 71.3, 70.4, 70.3, 70.2, 70.1, 70.0, 69.6, 69.3, 68.9, 68.4, 67.9, 66.1, 62.7, 62.4, 62.3, 62.1, 61.7, 61.3, 49.0, 46.8, 41.4, 36.6, 31.8, 31.5, 31.0, 30.2, 29.6, 29.2, 27.9, 26.2, 24.3, 22.6, 20.9, 20.8, 20.7, 20.6, 20.5. HRMS (MALDI) m/z Found: 2522.9401, calculated: 2522.9381 for $CH_{118}H_{156}N_5O_{53}S$ [M]+. Synthesis of MDP-2 To a stirred solution of 15 (50.0 mg, 0.02 mmol) in $CH_3OH$ (2 mL) was added aqueous LiOH (1.0 M, 2 mL), and the reaction mixture was stirred at room temperature for 24 hours. The mixture was then neutralized with Dowex 50W resin, filtered and concentrated in vacuo. The residue was purified by flash column chromatography on silica gel ($CH_2Cl_2/CH_3OH/H_2O$, 5/5/3) to afford MDP-2 (33.8 mg, quantitative). $^1$H NMR (400 MHz, $D_2O$): δ (ppm) 8.72 (d, 2H, J=12.8 Hz, ArH), 7.58 (s, 1H, Triazole) 7.33-7.29 (m, 4H, ArH), 7.20-6.93 (m, 4H, ArH), 6.11 (d, 2H, J=12.8 Hz, ArH), 5.43-5.40 (m, 5H), 4.48 (d, 1H, J=8.4 Hz, 1-H'), 4.33 (t, J=6.8 Hz, 2H), 4.17-4.09 (m, 3H), 4.05-3.45 (m, 60H), 3.41 (m, 1H), 3.35 (m, 1H), 2.88 (d, 2H, J=6.0 Hz, SCH2), 2.62 (m, 4H, C≡CCH2), 2.23-1.88 (m, 4H), 1.71 (s, 12H, CCH3). $^{13}$C NMR (100 MHz, $D_2O$): δ (ppm) 171.8, 153.9, 145.7, 143.2, 142.1, 140.3, 133.9, 128.2, 127.3, 127.0, 124.8, 121.9, 114.0, 110.1, 103.2 (β 1-C), 100.9, 100.7 (1-C), 100.3 (1-C), 100.2 (1-C), 77.9, 77.8, 75.4, 74.0, 73.9, 73.4, 72.5, 72.4, 72.3, 71.9, 70.0, 70.2, 68.3, 67.2, 62.7, 62.5, 62.2, 62.1, 61.8, 61.9, 58.5, 49.0, 48.2, 32.4, 29.9, 29.3, 27.9, 26.5. HRMS (MALDI) m/z Found: 1724.7398, calculated: 1724.7373 for $C_{80}H_{118}N_5O_{34}S+$ [M]+.

Mass spectrometry analysis of MDP-1 and MDP-2 with NanoSpray ionization-linear ion trap mass spectrometry (LTQ). MDP-1 and MDP-2 were suspended in methanol/water (1:1, 0.5 mg/mL) and infused directly into the LTQ instrument (LTQ, Thermo Finnigan) at a constant flow rate of 0.5 μL/min. The capillary temperature was set at 210° C. and MS analysis was performed in the positive ion mode. For tandom mass spectrometry experiments, the collision energy was set to 35~45%, the m/z ranged from 400 to 2000, and was scanned with 2.2 mass units per window. The tandom mass spectrometry results of MDP-1 confirm the structure of MDP-1. The MS/MS data of m/z 1416 show a glucose-loss ladder and the loss of other fragments such as N2 and perylene dye, which matches with the predicted fragmentation pattern of MDP-1. The tandom mass spectrometry results of MDP-2 confirm the structure of MDP-2. The MS/MS data of m/z 1725 show a glucose-loss ladder and the loss of other fragments such as N2 and IR786 dye, which matches with the predicted fragmentation pattern of MDP-2.

Example 2

Uptake of MDP-1 and MDP-2 In Vitro

The uptake of MDP-1 and MDP-2 was investigated in *E. coli* (ATCC 33456), *P. aeruginosa* (ATCC 47085), *B. subtilis* (ATCC 23059), *S. aureus* (ATCC 6538), metabolically inactive *E. coli* (sodium azide-treated) and two *E. coli* mutant strains, which contained either a LamB mutation (JW3992-1) or a MalE mutation (TL212). All bacteria were cultured overnight in Luria-Bertani medium at 37° C. under 5% $CO_2$ in an incubator shaker (Innova 4230, New Brunswick Scientific). Bacteria (100 μl from the overnight culture) were re-suspended in 30 ml fresh Luria-Bertani medium and cultured to an attenuance $D_{600\ nm}$=0.5 in a 250 ml flask in an incubator shaker. Bacteria (3 ml) at steady-state growth were transferred into six-well plates and incubated with 20 μM MDP-1 or MDP-2 in Luria-Bertani medium in an incubator shaker at 37° C. for 1 h. The bacteria were centrifuged at 10,000 r.p.m. for 15 min in 15 ml centrifuge tubes, using a Microfuge 18 centrifuge (Beckman Coulter). The recovered bacterial pellets were washed three times with 10 ml PBS. The bacteria were lysed in 2 ml deionized water by sonication with a Branson Sonifier S-250A (Branson Ultrasonics Corporation), using a constant duty cycle at a 200 W output;

10 sonication cycles were performed. The bacterial supernatant (diluted in a 2 ml volume) was isolated by centrifuging at 10,000 r.p.m. for 10 min. The fluorescence intensity of the supernatant was measured in a Shimadzu spectrofluorometer (RF 5301 PC) and normalized to either the bacterial protein content or the bacterial cell volume.

MDP-1 was internalized through the maltodextrin transporter. Experiments were performed with LamB mutant *E. coli* (LamB mutants) to determine whether MDP-1 was internalized through the maltodextrin transporter. LamB mutants were incubated with MDP-1 and the internalization of MDP-1 was determined. FIG. 3a demonstrates that LamB mutants do not internalize MDP-1 and that, therefore, MDP-1 enters *E. coli* through the maltodextrin transport pathway. The uptake of MDP-1 in wild-type *E. coli* could also be inhibited by an excess of maltose or maltohexaose, further confirming that MDP-1 is internalized by maltodextrin transporters. FIG. 3a shows that metabolically inactive bacteria do not accumulate MDP-1, demonstrating that MDP-1 is not binding to the bacteria cell surface through non-specific interactions.

The uptake of MDPs in bacteria and mammalian cells was determined and compared. Bacteria (*E. coli, P. aeruginosa, B. subtilis* and *S. aureus*) and mammalian cells (rat aortic smooth muscle cells, macrophages and fibroblasts) were incubated with a 20 µM concentration of MDP-1 for 1 h, washed with PBS, lysed, and the cellular supernatant was analysed for perylene fluorescence signal. FIG. 3c shows that MDP-1 has high specificity for bacteria. For example, both gram-positive and gram-negative bacteria internalized MDP-1 at a rate three orders of magnitude faster than mammalian cells. In particular, pathogenic bacteria such as *P. aeruginosa* and *S. aureus* internalized 200-300 µmol of MDP-1 per milligram of protein, whereas rat aortic smooth muscle cells and fibroblasts internalized undetectable levels of MDP-1. Furthermore, MDP-2 has a similarly high level of specificity for bacteria when compared with mammalian cells. MDPs have a thousand times better selectivity for bacteria when compared with mammalian cells and should therefore be able to detect bacteria in vivo with high specificity.

Example 3

Uptake of MDP-1 in Bacterial Biofilms

Experiments were performed to determine whether MDPs could target bacterial biofilms, a major source of pathology from infectious diseases. Although bacterial biofilms have a significantly altered physiology in comparison with planktonic bacteria, they still consume glucose, and therefore can potentially be imaged by MDPs. The ability of MDP-1 to image bacterial biofilms was investigated. Biofilms were incubated with a 20 µM concentration of MDP-1 for 10 min, and counter-stained with SYTO59, a long-wavelength cell-permeable nucleic acid stain. FIG. 3d demonstrates that MDP-1 is actively taken up by a wide variety of bacterial biofilms. In particular, biofilms formed from *E. coli* (12±4 µm thickness), *P. aeruginosa* (24±15 µm thickness), *B. subtilis* (16±7 µm thickness) and *S. aureus* (51±30 µm thickness) all avidly internalized MDP-1, demonstrating that maltodextrin transporters are active in bacterial biofilms and can potentially be used in diagnosing diseases associated with bacterial biofilms.

Example 4

In Vivo Imaging of Bacterial Infections with MDP-2

Figure 4:
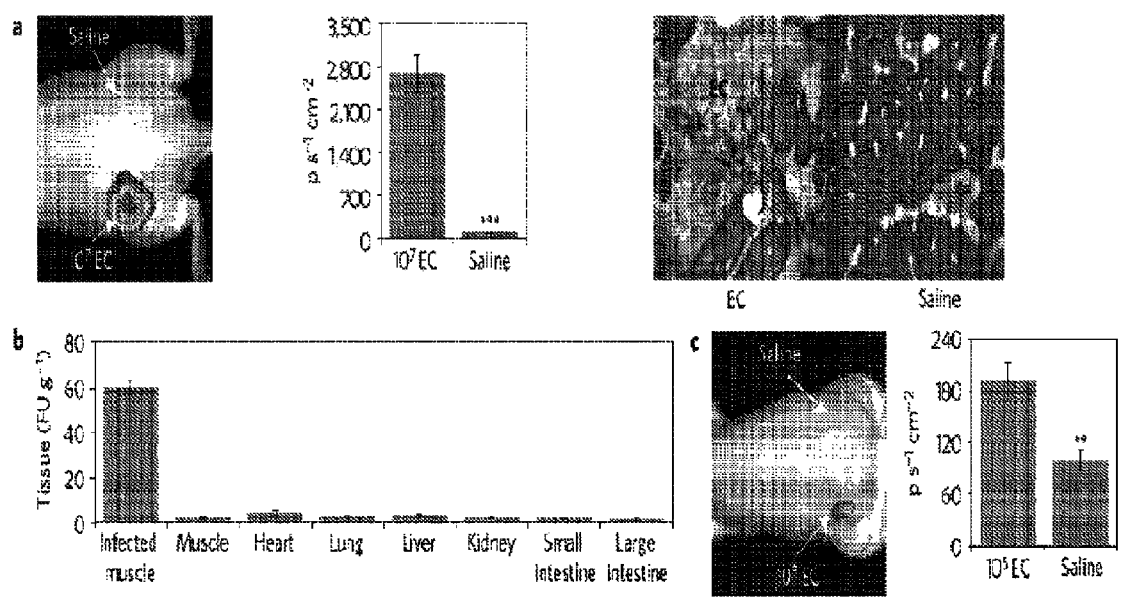
FIG. 4 shows MDP-2 images bacteria in vivo. a Left: fluorescence image of a rat showing that MDP-2 can image $10^7$ *E. coli* CFUs in vivo. Middle: histogram showing quantification of fluorescence intensity. *E. coli* ($10^7$ CFUs) infected muscles have a 26-fold increase in fluorescence intensity when compared with uninfected control muscles. Right: micrograph of the histology of *E. coli*-injected thigh muscles showing that bacteria are present in infected muscles (×20 magnification). b, Histogram showing MDP-2 distribution in rats infected with *E. coli*. MDP-2 is efficiently cleared from all the major organs and selectively accumulates in infected muscle tissue. Data are plotted as mean fluorescent units (FUs) per gram of tissue±s.e.m. (n=6 rats per group). The p values between the infected muscle and the other tissues were determined by a one-way ANOVA using Bonferroni's post-hoc test, and were found to be statistically significant (p≤0.001). c Left: fluorescence image of a rat showing that MDP-2 can image $10^5$ *E. coli* CFUs in vivo. Right: histogram showing quantification of fluorescence intensity. *E. coli* ($10^5$ CFUs) infected muscles have a twofold increase in fluorescence intensity when compared with uninfected control muscles. The rat images in a left and c left are representative results of six experiments. Regions of interest (ROI) in a left and c left were identified and integrated using software from the Lumina machine. The results in a middle and c middle are expressed as mean numbers of photons per second per $cm^2$ in the designated ROI±s.e.m. for n=6 per group. The statistical significances in a middle and c middle were determined using a two-sample Student t-test (p≤0.01 and *p≤0.001).
Figure 5:
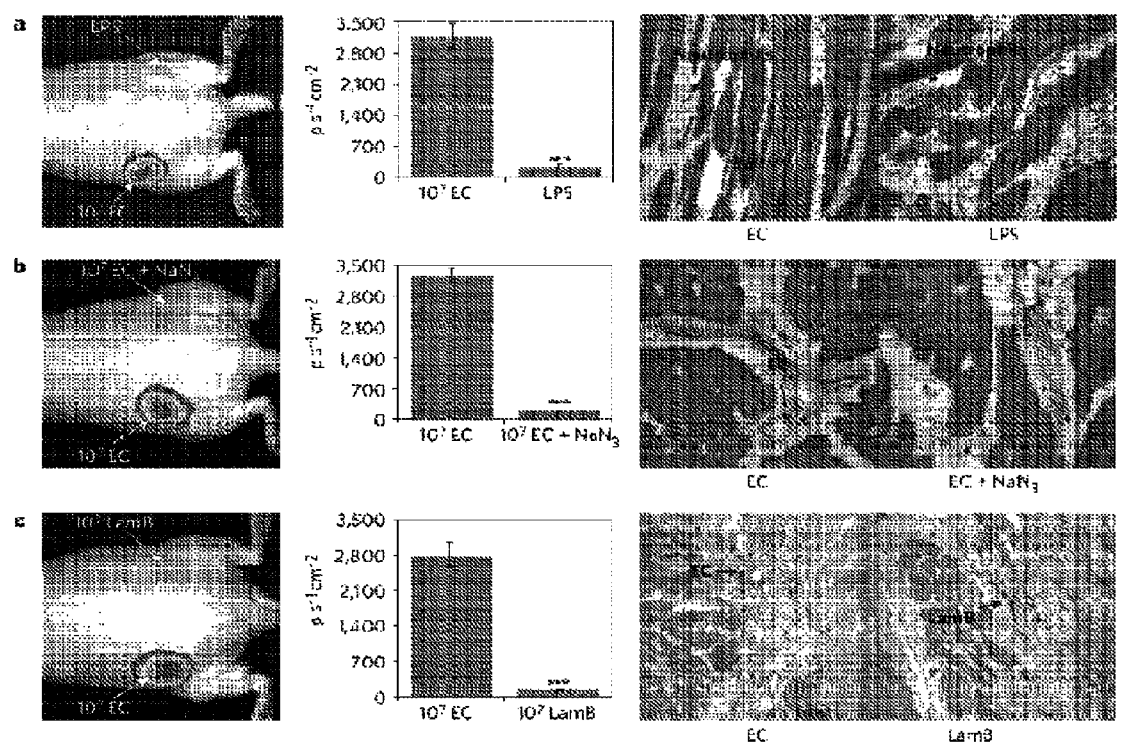
FIG. 5 shows data indicating MDP-2 images bacteria in vivo using internalization through the maltodextrin transporter. a Left: image showing that MDP-2 can distinguish between *E. coli* infection ($10^7$ CFUs) and LPS (1 mg $kg^{-1}$)-induced inflammation. Middle: histogram showing quantification of fluorescence intensity. *E. coli*-infected tissues had a 17-fold increase in fluorescence intensity when compared with LPS-treated tissues. Right: micrograph showing the histology of *E. coli*- and LPS-treated muscles demonstrating that both *E. coli* and LPS induce a large amount of inflammation (×20 magnification). b Left: image showing that MDP-2 is actively transported by bacteria in vivo, and does not accumulate in metabolically inactive bacteria. Middle: histogram showing quantification of fluorescence intensity. *E. coli*-infected tissues have an 18-fold increase in fluorescence intensity when compared with tissues treated with metabolically inactive bacteria. Right: image showing the histology of thigh muscles injected with either *E. coli* or metabolically inactive *E. coli* demonstrating that bacteria are present (×20 magnification). c Left: image showing that MDP-2 is transported by bacteria in vivo, through the maltodextrin transport pathway, and does not accumulate in LamB mutants. Middle: histogram showing quantification of fluorescence intensity. *E. coli*-infected tissues have a 20-fold increase in fluorescence intensity when compared with tissues treated with LamB-negative *E. coli*. Right: image showing histology of thigh muscles injected with either *E. coli* or LamB mutants demonstrating that bacteria are present in infected muscles (×20 magnification). The rat images in a left, b left and c left are representative results of six experiments. Regions of interest in a left, b left and c left were identified and integrated using software from the Lumina machine. The results in a middle, b middle and c middle are expressed as mean numbers of photons per second per $cm^2$ in the designated ROI±s.e.m. for n=6 per group. The statistical significances in a middle, b middle and c middle were determined using a two-sample Student t-test (***p≤0.001).

MDPs have the potential to image bacteria in vivo. The ability of MDP-2 to image bacterial infections in rats was investigated. The rats were injected in the left and right thigh muscles, respectively, with *E. coli* ($10^7$ colony-forming units, CFUs) and saline (as a control). After 1 h the rats were injected with MDP-2 (280-3501 of 1 mM MDP-2 in PBS) through the jugular vein and imaged after 16 h in an IVIS imaging machine. FIG. 4a shows that MDP-2 can image bacterial infections in vivo. For example, rat thigh muscles infected with *E. coli* had a 26-fold increase in fluorescence intensity when compared with uninfected controls, allowing the infected area to be easily visualized in vivo. The ability of MDP-2 to target bacteria in vivo was quantified by performing a biodistribution study of MDP-2 in rats infected with *E. coli* ($10^7$ CFUs). FIG. 4b demonstrates that MDP-2 accumulates in infected muscle tissues and is efficiently cleared from uninfected muscle, having a 42-fold increase in fluorescence intensity between infected and uninfected muscle tissues. MDP-2 did not accumulate in the bacterial microflora of colon tissue, presumably because of the impermeability of the lumen tissue of intestinal tissues to glucose oligomers. MDP-2 was also efficiently cleared from all the major organs, indicating that it could potentially be used for imaging infections in a wide range of tissues.

Female Wistar rats (10 weeks, 200-250 g, Harlan Laboratories) were anaesthetized with isofluorane and the hair on the thigh and back was removed. A suspension of *E. coli* ($10^5$-$10^7$ CFUs) in 250 µL saline was injected into the left rear thigh muscle (injection depth 5 mm), and 250 µL of saline was injected into right rear thigh muscle as a control (injection depth 5 mm). After 1 h the rats were injected with MDP-2 (280-350 µL of 1 mM MDP-2 in PBS) through the jugular vein. Fluorescence images were captured using an IVIS Lumina Imaging System (Caliper Life Sciences) 16 h after the MDP-2 injection. The fluorescence intensity from the bacteria or saline injection area (region of interest) was integrated. At the end of the imaging procedure rats were euthanized, by $CO_2$ inhalation, and the bacterial infected and saline-treated muscles were collected and analyzed by histology for the presence of bacteria. Six rats were used for each experimental group.

Example 5

The Uptake of MDP-1 in the Presence of Antibiotics

The ability of antibiotics to inhibit the uptake of MDP-1 in *Escherichia coli* was investigated. *Escherichia coli* (ATCC 33456) were grown in LB medium at 37° C. under 5% $CO_2$ to an OD600=0.5, as described above. 3 mL of this bacterial suspension was transferred to 6 well plates, preincubated at 37° C. for 5 minutes under shaking (as described above), and 30 μL of various concentrations of ampicillin stock solutions (0.3, 0.6, 1.2, and 1.8 mg/mL in PBS) were added, generating a 3 ($IC_{50}$), 6, 12 and 18 μg/mL final concentration of ampicillin. *Escherichia coli* were incubated with ampicillin for 1 hour at 37° C. under 5% $CO_2$, and 60 μL of MDP-1 stock solutions (1 mM in PBS) were added, generating a 20 μM MDP concentration. *Escherichia coli* were incubated with MDPs in the presence of ampicillin for 1 hour at 37° C. under 5% $CO_2$ in an incubator shaker. At this stage, a small aliquot of the bacterial culture was plated to determine the CFUs of bacteria in the MDP solution. *Escherichia coli* were harvested by centrifuging and the resulting pellets were washed 3 times with 10 mL PBS. The intracellular fluorescence of the bacteria was determined as described in FIG. 3*a*. The results demonstrate that the maltodextrin transporter in *Escherichia coli* is still active in the presence of antibiotics.

Example 6

In Vivo Imaging of Bacterial Infections with $MH^{18}F$

A PET imaging agent, termed $MH^{18}F$ can diagnose bacterial infections in vivo at an early stage, with high specificity. $MH^{18}F$ has several unique properties that give it the potential to image early stage infections with specificity. In particular, $MH^{18}F$ is rapidly internalized by bacteria, through the maltodextrin transport pathway, but is not internalized by mammalian cells because they do not have maltodextrin transporters. In addition, $MH^{18}F$ is composed of glucose oligomers, which are hydrophilic and membrane impermeable, and is efficiently cleared from un-infected tissues in vivo, leading to low background. Maltohexaose can be labeled with $^{18}F$ and can image bacterial infections in rats with high specificity and sensitivity. See FIG. 12. $^{18}F$ labeled contrast agents based on targeting the maltodextrin transport pathway will image bacterial thigh infections in rats at an early stage ($10^7$ CFUs), distinguish between infection and inflammation, detect the presence of drug resistant bacteria, and diagnose bacterial infections.

Figure 11:
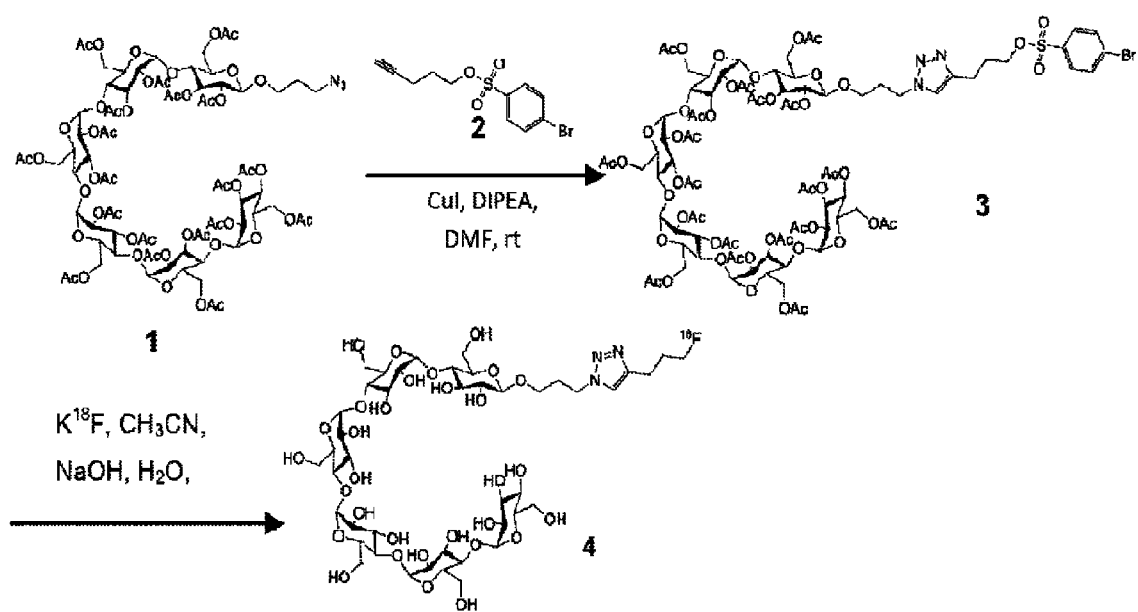
FIG. 11 schematically illustrates the synthesis of $MH^{18}F$.

Synthesis of brosylated maltohexaose (3). See FIG. 11. To a stirred solution of 4 (57.0 mg, 0.03 mmol) and 3 (19.0 mg, 0.06 mmol) in DMF (5 mL) was added CuI (0.3 mg, 1.5 mol) and DTPEA (1.2 mg, 0.01 mmol). The mixture was stirred at room temperature for 24 hours under nitrogen and the solvent was removed in vacuo. The residue was dissolved in $CH_2Cl_2$ (25 mL) and washed with water (5 mL×2) and brine (5 mL). The organic phase was dried over $Na_2SO_4$, filtered and evaporated to dryness in vacuo. The residue was purified by flash column chromatography on silica gel (hexane/acetone, 2/3) to afford 5 (45.0 mg, 69.2%). $^1H$ NMR (400 MHz, $CDCl_3$): δ (ppm) 7.78 (d, 2H, J=8.0 Hz, ArH), 7.70 (d, 2H, J=8.0 Hz, ArH), 7.45 (br, 1H, triazole), 5.41-5.25 (m, 11H), 5.05 (t, 1H, J=10.0 Hz, 4"-H), 4.85 (dd, 1H, J=4.0 and 10.0 Hz, α 2'-H), 4.71→4.68 (m, 3H), 4.47-3.52 (m, 56H), 2.17-1.88 (m, 61H), 1.55-1.44 (m, 4H, CH2). $^{13}C$ NMR (100 MHz, $CDCl_3$): δ (ppm) 170.6, 170.6, 170.6, 170.5, 170.5, 170.4, 170.3, 170.3, 170.3, 170.0, 169.7, 169.6, 169.6, 169.5, 169.4, 169.4 (C=O), 155.3, 154.6, 152.3, 152.2, 145.4, 125.3, 121.8, 121.7, 101.3, 100.2 (β 1-C), 95.7 (1-C), 95.7 (1-C), 95.6 (1-C), 76.7, 75.2, 73.7, 73.2, 72.4, 72.3, 72.1, 71.7, 71.6, 71.3, 70.4, 70.3, 70.2, 70.1, 70.0, 69.6, 69.3, 68.9, 68.4, 67.9, 66.1, 62.7, 62.4, 62.3, 62.1, 61.7, 61.3, 49.0, 46.8, 41.4, 38.2, 37.8, 37.1, 37.0, 36.7, 29.3, 20.8, 20.7, 20.6, 20.5. HRMS (MALDI) m/z Found: 2196.5301, calculated: 2196.5276 for $C_{88}H_{116}N_3O_{53}SNa$ $[M+Na]^+$.

Synthesis of $MH^{18}F$ (4) was performed. See FIG. 11. $^{18}F$— (obtained via the $^{18}O$ (p,n) $^{18}F$ nuclear reaction by bombardment of enriched [$^{18}O$]water (94%) with a 17 MeV proton beam) was passed through an anion exchange resin and [$^{18}O]H_2O$ was recovered. $^{18}F$— was eluted with aqueous potassium carbonate. An aliquot of this solution containing the desired quantity of radioactivity was transferred to a reaction vial. The water was evaporated under reduced pressure at 110° C. and dried by co-evaporation with acetonitrile. A solution of brozylate-maltohexaose 5 (10 mg, 5.0 μmol) in 0.5 mL anhydrous acetonitrile was added and the mixture was heated for 30 min at 110° C. The reaction mixture was concentrated with gentle heating under a stream of Ar gas. The residue was then mixed with 0.5 ml of 1N NaOH aqueous solution and the resulting mixture was heated for 10 min at 110° C. After cooling, the mixture was neutralized with 1N HCl and the solution was passed over a small ion exchange column to provide radioactive $MH^{18}F$ (2-3 mCi). The collected radioactive solution was analyzed by radio-TLC (5:1 acetonitrile:water; Rf=0.5).

Figure 12:
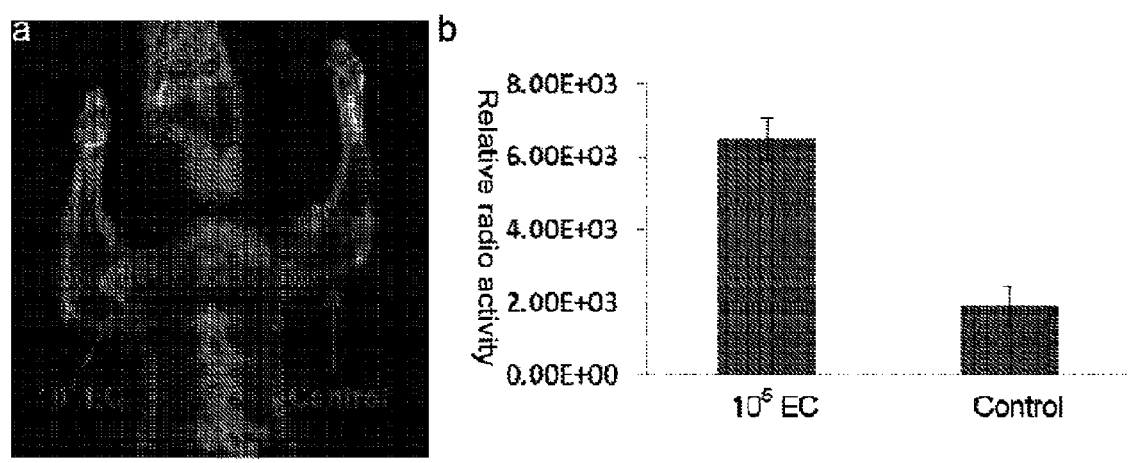
FIG. 12 indicates that $MH^{18}F$ images bacteria in vivo using micro PET/CT scanner. a, $MH^{18}F$ can image $10^5$ EC in vivo. Rats were infected with EC ($10^5$ CFUs) and imaged 90 min after the injection of $MH^{18}F$. b, EC ($10^5$ CFUs) infected left tricep muscles have a 4 fold increase in relative radio activity over un-infected right control muscles.

In vivo imaging of bacterial infections with $MH^{18}F$ was evaluated. The ability of $MH^{18}F$ to detect bacteria in vivo was determined using a micro PET/CT scanner. Female Sprague Dawley rats (10 weeks, 200-250 g, Charles River Lab, Inc.) were anaesthetized with ketamine (60 mg/kg) and xylazine (10 mg/kg) via an intramuscular (IM) injection. A suspension of *Escherichia coli* (EC) ($10^9$ CFUs) in 250 μL saline was injected into the left tricep muscle (injection depth 5 mm), and 250 μL of saline was injected into right tricep muscle as a control (injection depth 5 mm). After 2 hour the rats were injected with $MH^{18}F$ (100 μL of 10 mM $MH^{18}F$ in PBS) via the tail vein. PET images were acquired 90 minutes using an Inveon Micro PET/CT Preclinical Scanner (Siemens) right after the $MH^{18}F$ injection, and the photon counts emanating from the bacteria or saline injection area (region of interest) were integrated. FIG. 12 demonstrates that $MH^{18}F$ can image bacterial infections in vivo using a micro PET/CT scanner. Rat tricep muscles infected with *Escherichia coli* had an 11 fold increase in relative radioactivity over un-infected controls, allowing the infected area to be easily visualized in vivo.

Figure 13:
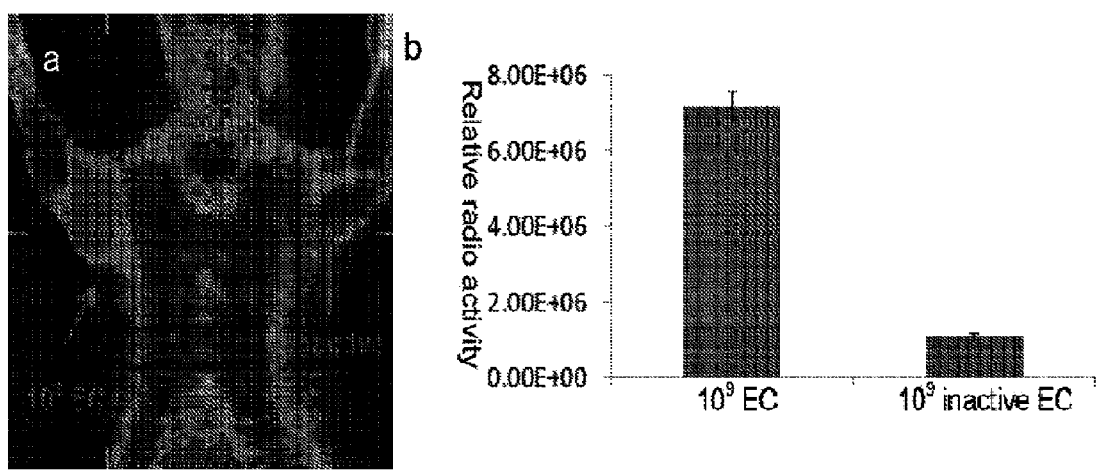
FIG. 13 indicates that $MH^{18}F$ can distinguish bacterial infections from inflammation. a, $MH^{18}F$ can distinguish between bacterial infections and metabolically inactive bacteria induced inflammation. Rats were infected with EC ($10^9$ CFUs) in the left tricep muscle and metabolically inactive EC ($10^9$ CFUs) in the right thigh muscle, and imaged 90 min after the injection of $MH^{18}F$. b, EC infected tissues had a 9 fold increase in radio activity over inflamed tissues.

Imaging early stage *E. coli* bacterial infections with $MH^{18}F$ was evaluated. EC ($10^5$ CFUs) were injected into the left tricep muscle of rats and imaged with $MH^{18}F$ as described above. FIG. 12 demonstrates that $MH^{18}F$ is capable of detecting as few as $10^5$ bacterial CFUs in vivo. For example, rat tricep muscles infected with $10^5$ bacterial CFUs had a 4 fold increase in relative radioactivity over un-infected controls. Detection of 10 CFUs in a clinical setting would represent a significant increase in current infection diagnostic ability, which can generally only detect infections that are on the order of 1 $cm^3$ in volume, between $10^9$-$10^{12}$ CFUs. $MH^{18}F$ can distinguish between bacterial infections and sterile inflammation. Rats were injected with $10^9$ CFUs of EC in the left tricep muscle and metabolically inactive EC in the right tricep muscle, and then imaged with MH$^{18}$F as described above. FIG. 13 demonstrates that MH$^{18}$F can distinguish between bacterial infections and inflammation with high specificity. Rat tricep muscles infected with EC had a 9 fold increase in relative radioactivity over inflamed tissues.

Example 7

Maltodextrin Conjugates are Internalized by a Wide Variety of Bacteria

Figure 14:
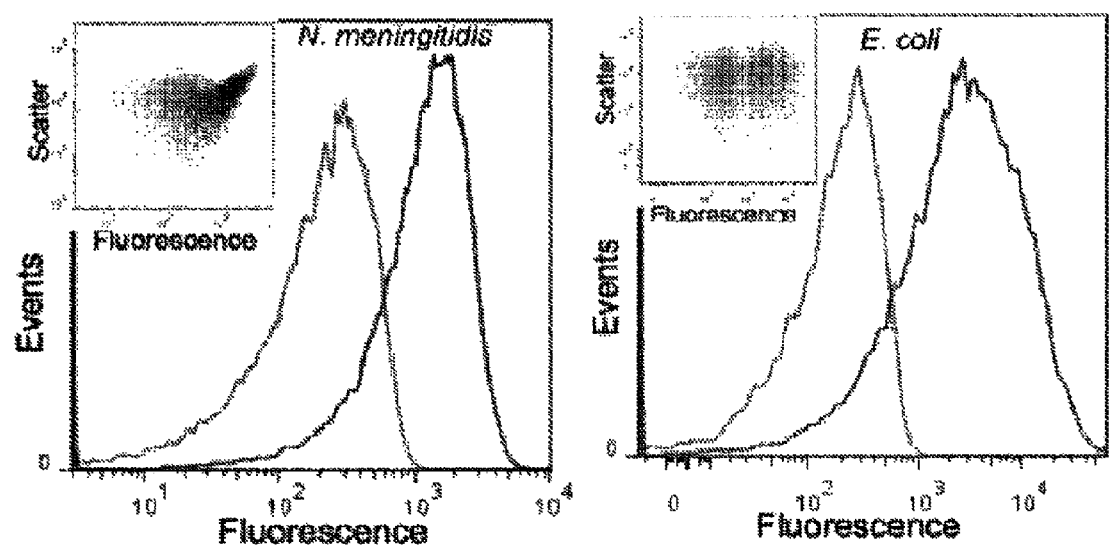
FIG. 14 shows data indicating *N. meningiditis* internalizes MDP-1, even though it lacks classical maltodextrin transporters. Flow cytometry discrimination of MDP-1 uptake in *E. coli* (left) and *N. meningitidis* (right), excited at 405 nm. For both panels, red and blue data are bacteria alone, or those incubated with 20 µM MDP-1, respectively. Insets: dot plots of side scatter vs fluorescence clearly shows differences between 20 µM MDP-1 incubation and negative control populations for *E. coli* (left) and *N. meningitidis* (right).

A protein sequence homology search was performed for the presence of classical maltodextrin transporters, such as LamB and/or MalE in common infectious pathogens. Maltodextrin transporters or highly homologous maltose transport systems were identified in *Citrobacter koseri, Enterobacter* sp., *E. coli* species, *Klebsiella pneumoniae, Salmonella* species, *Shigella flexneri, Shigella sonnei, Vibrio vulnificus,* and *Vibrio cholerae*. Bacteria may also internalize maltodextrins via non-classical maltodextrin transport systems, and have demonstrated that *P. aeruginosa* robustly internalizes MDP-1. In addition, whether *Neisseria meningitidis*, a gram negative pathogen that does not express classical maltodextrin transporters, internalizes MDP-1 via flow cytometry, was investigated following the procedures described above. FIG. 14 demonstrates that *Neisseria meningitidis* robustly internalized MDP-1, and internalizes it at a rate similar to that of *E. coli*, supporting the notion that a wide range of bacteria can potentially internalize maltodextrin based conjugates.

Example 8

Antibiotic Conjugates of Maltodextrin

Figure 15:
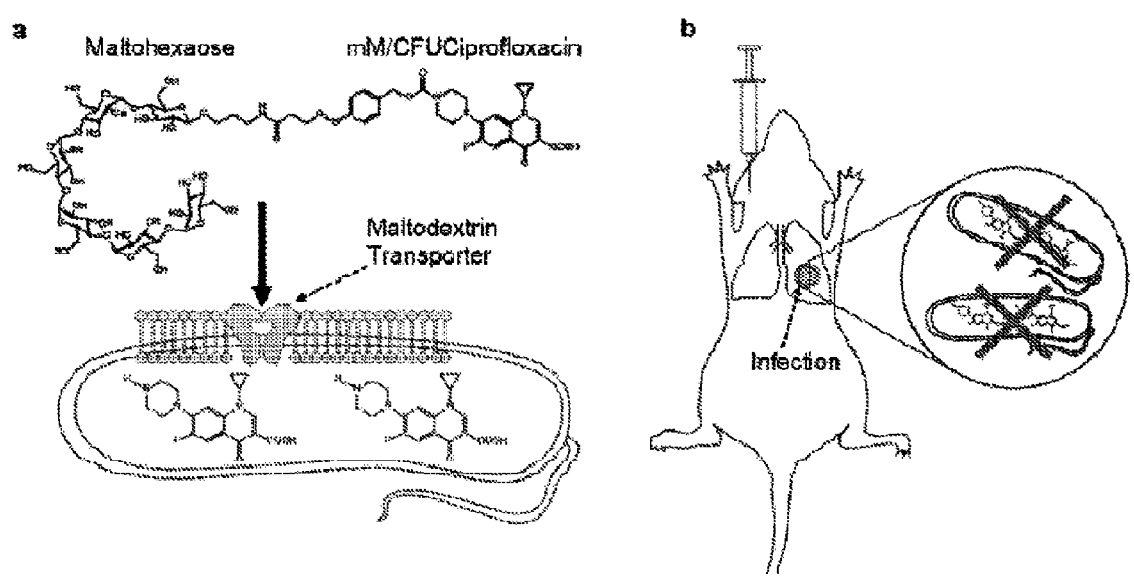
FIG. 15 illustrates maltodextrin conjugated ciprofloxacin (MDC) as a strategy for targeting therapeutics to drug resistant bacteria. a, Chemical design of the MDCs. MDCs are composed of maltohexaose conjugated to ciprofloxacin, and are internalized by bacteria at a high rate due to transport by the maltodextrin transporter. b, MDCs treat drug resistant bacterial infections. MDCs are robustly internalized by bacteria but not by mammalian cells, allowing for high doses to be administered with low toxicity, enabling effective treatment of drug resistant bacteria.
Figure 16:
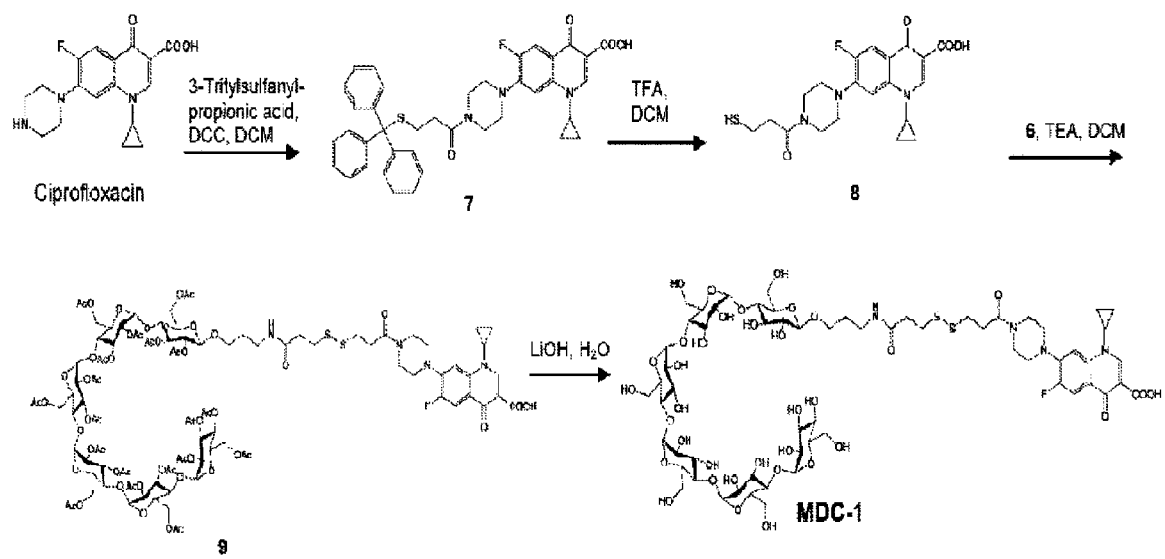
FIG. 16 schematically illustrates the preparation of an example of a ciprofloxacin and maltohexaose conjugate.

Maltohexaose can be conjugated to ciprofloxacin, generating MDC-1. See FIG. 15. This conjugate can be internalized by *E. coli* and kill *E. coli*. The transport kinetics of MDC-1 will be investigated in the PAO1 *P. aeruginosa* strain, and the ability of MDC-1 to kill *P. aeruginosa* will be investigated, and compared against free ciprofloxacin. It is desired that MDC-1 has a wider therapeutic window than free ciprofloxacin at treating drug resistant *P. aeruginosa* and *Staphylococcus aureus* muscle infections. The ability of MDC-1 to rescue rats from *P. aeruginosa* will be investigated and compared against free ciprofloxacin. A muscle model of infection will be used for these studies. The therapeutic window of MDCs against *P. aeruginosa* will be determined. $^{14}$C-labeled MDC-1 will also be synthesized and their ability to target *P. aeruginosa* in rats will be investigated and compared against $^{14}$C-labeled ciprofloxacin.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:
1. A composition comprising a positron-emitting radionuclide conjugated to maltodextrin.
2. The composition of claim 1, wherein the positron-emitting radionuclide is selected from carbon-11, nitrogen-13, oxygen-15, fluorine-18, rubidium-82, and strontium-82.
3. The composition of claim 1, wherein the maltodextrin has greater than 2 glucose oligomers.
4. The composition of claim 1, wherein the composition is

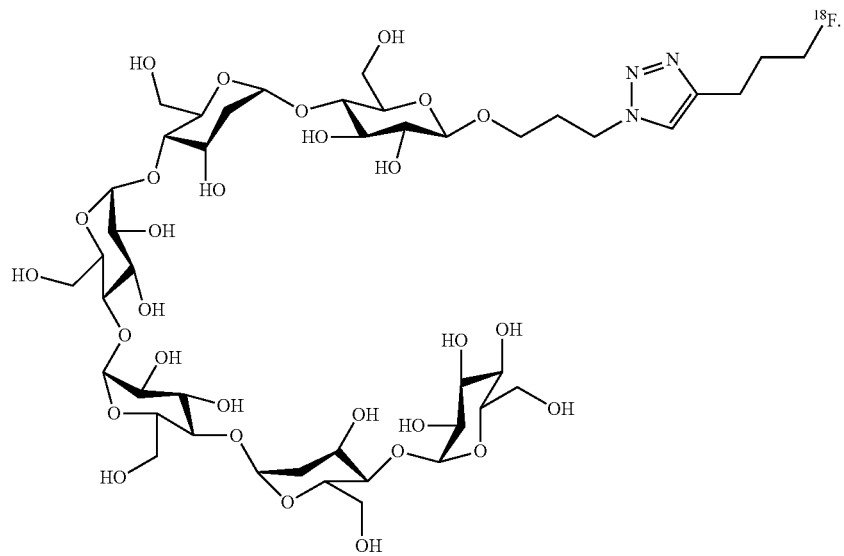

* * * * *

UNITED STATES PATENT AND TRADEMARK OFFICE
CERTIFICATE OF CORRECTION

PATENT NO.        : 9,821,071 B2                        Page 1 of 1
APPLICATION NO.   : 14/190928
DATED             : November 21, 2017
INVENTOR(S)       : Niren Murthy It is certified that error appears in the above-identified patent and that said Letters Patent is hereby corrected as shown below:

In the Claims

Please replace Column 30, Claim 4, Lines 38 through 40, with the following, correcting the formula:
"The composition of Claim 1, wherein the composition is

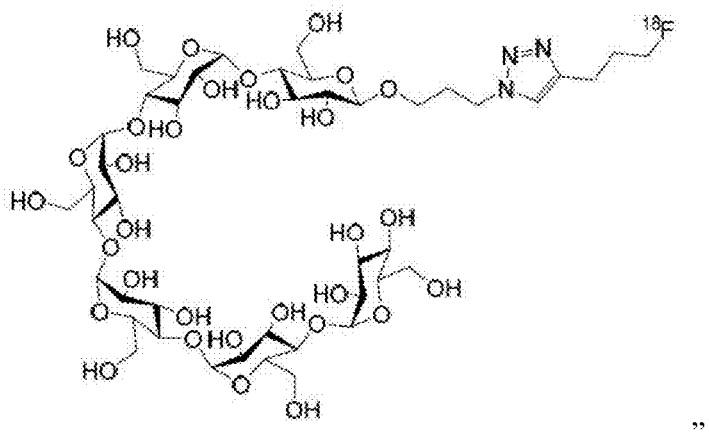

"

Signed and Sealed this
Twenty-ninth Day of May, 2018

Andrei Iancu
*Director of the United States Patent and Trademark Office*